US006698422B2

(12) United States Patent
Fugelsang et al.

(10) Patent No.: US 6,698,422 B2
(45) Date of Patent: Mar. 2, 2004

(54) CANISTER INHALER HAVING A SPACER AND EASY TO OPERATE LEVER MECHANISM AND A FLEXIBLE, ELASTIC MOUTHPIECE

(75) Inventors: Eric Fugelsang, Greenwich, CT (US); Martin Muszak, Rochester, NY (US)

(73) Assignee: Birdsong Medical Devices, Inc., Brewster, NY (US)

( * ) Notice: Subject to any disclaimer, the term of this patent is extended or adjusted under 35 U.S.C. 154(b) by 0 days.

(21) Appl. No.: 10/084,215

(22) Filed: Feb. 25, 2002

(65) Prior Publication Data

US 2002/0157664 A1 Oct. 31, 2002

Related U.S. Application Data

(63) Continuation-in-part of application No. 09/804,508, filed on Mar. 12, 2001, now Pat. No. 6,523,536.

(51) Int. Cl.[7] .............................................. A61M 11/00
(52) U.S. Cl. ........................... 128/200.14; 128/200.22; 128/200.23
(58) Field of Search .................. 128/200.14, 200.22, 128/200.23, 203.11, 203.12, 200.19; 222/162, 182, 183

(56) References Cited

U.S. PATENT DOCUMENTS

| | | | | |
|---|---|---|---|---|
| 3,405,843 A | * | 10/1968 | Watson, Jr. | |
| 3,456,645 A | * | 7/1969 | Brock | |
| 3,625,403 A | * | 12/1971 | Rousselot | 128/200.23 |
| 3,718,234 A | * | 2/1973 | Bagguley | 222/162 |
| 3,826,413 A | * | 7/1974 | Warren | 128/200.23 |
| 4,079,862 A | * | 3/1978 | Fegley | 222/162 |
| 4,324,348 A | * | 4/1982 | Johnson et al. | 222/183 |
| 4,402,430 A | * | 9/1983 | Fox et al. | 222/183 |
| 4,470,412 A | * | 9/1984 | Nowacki et al. | 128/200.23 |
| 4,534,343 A | * | 8/1985 | Nowacki et al. | 128/200.23 |
| 4,678,106 A | * | 7/1987 | Newell et al. | 128/200.23 |
| 4,790,305 A | | 12/1988 | Zoltan et al. | 128/200.23 |
| 4,809,692 A | | 3/1989 | Nowacki et al. | 128/206.24 |
| 4,832,015 A | | 5/1989 | Nowacki et al. | 128/205.23 |
| 4,852,561 A | * | 8/1989 | Sperry | 128/200.23 |
| 4,860,738 A | * | 8/1989 | Hegemann et al. | 128/200.22 |
| 4,863,443 A | * | 9/1989 | Hornung | 128/200.14 |
| 4,926,852 A | | 5/1990 | Zoltan et al. | 128/200.23 |
| 5,002,048 A | * | 3/1991 | Makiej, Jr. | 128/200.23 |
| 5,007,419 A | * | 4/1991 | Weinstein et al. | 128/200.23 |
| 5,012,803 A | | 5/1991 | Foley et al. | 128/200.23 |
| 5,012,804 A | | 5/1991 | Foley et al. | 128/200.23 |
| 5,040,527 A | | 8/1991 | Larson et al. | 128/200.23 |
| 5,042,467 A | | 8/1991 | Foley | 128/200.23 |
| 5,169,029 A | * | 12/1992 | Behar et al. | 222/162 |
| 5,184,761 A | * | 2/1993 | Lee | 222/182 |

(List continued on next page.)

OTHER PUBLICATIONS

WE Pharmaceuticals, Inc. E–Z Spacer & E–Z Spacer Mask (Small).*

(List continued on next page.)

Primary Examiner—Aaron J. Lewis
(74) Attorney, Agent, or Firm—Kenyon & Kenyon

(57) ABSTRACT

The present invention relates to an inhaler for effectively delivering medications by inhalation through the mouth of patients, having a spacer for more effectively mixing the medication and air, and easy to operate lever and canister selection mechanisms. A preferred embodiment of the invention has a mouthpiece comprising a flexible, elastic material. A lever arm is provided that is opposed to the body of the inhaler, which allows a patient to use the entire hand to activate the metered dose inhaler canister. In a preferred embodiment a valve assembly and whistle are included in the inhaler to improve the consistency and effectiveness of delivery of medication to the lungs of a patient.

34 Claims, 13 Drawing Sheets

U.S. PATENT DOCUMENTS

| | | | | |
|---|---|---|---|---|
| 5,349,947 A | * | 9/1994 | Newhouse et al. | 128/203.21 |
| 5,385,140 A | | 1/1995 | Smith | 128/200.23 |
| 5,427,089 A | | 6/1995 | Kraemer | 128/200.23 |
| 5,645,049 A | | 7/1997 | Foley et al. | 128/203.29 |
| 5,816,240 A | | 10/1998 | Komesaroff | 128/200.23 |
| 5,848,588 A | | 12/1998 | Foley et al. | 128/200.23 |
| 5,988,160 A | | 11/1999 | Foley et al. | 128/200.22 |
| 6,026,807 A | | 2/2000 | Puderbaugh et al. | 128/200.23 |
| 6,039,042 A | * | 3/2000 | Sladek | 128/200.23 |
| 6,071,498 A | | 6/2000 | Narodylo et al. | 424/46 |
| 6,125,844 A | | 10/2000 | Samiotes | 128/200.23 |
| 6,293,279 B1 | * | 9/2001 | Schmidt et al. | 128/200.23 |
| 6,345,617 B1 | * | 2/2002 | Engelbreth et al. | 128/200.18 |
| 6,435,177 B1 | * | 8/2002 | Schmidt et al. | 128/200.18 |
| 6,453,900 B1 | | 9/2002 | Barnes et al. | 128/200.23 |

OTHER PUBLICATIONS

Demirkan et al., "Salmeterol Administration by Metered Dose Inhaler Alone vs. Metered Dose Inhaler Plus Valved Holding Chamber", Chest, V. 117 (2000) pp. 1314–1318.*

Fnlay and Zuberbuhler, "In Vitro Comparison of Beclomethasone and Salbuterol Metered Dose Inhaler Aerosols Inhaled During Pediatric Tidal Breathing from Four Valved Holding Chambers", Chest, V. 114 (1988) pp. 1676–1680.*

Konig, "Spacer Devices Used with Metered Dose Inhalers. Breakthrough or Gimmick?", Chest V.88 (1985), pp. 276–284.*

* cited by examiner

CANISTER INHALER HAVING A SPACER AND EASY TO OPERATE LEVER MECHANISM AND A FLEXIBLE, ELASTIC MOUTHPIECE

This is a continuation-in-part of application Ser. No. 09/804,508, filed Mar. 12, 2001 now U.S. Pat. No. 6,523,536.

FIELD OF THE INVENTION

The present invention relates to a canister inhaler for effectively delivering medications by inhalation through the mouth of patients having a flexible, elastic mouthpiece, a spacer for more effectively mixing the medication and air, and an easy to operate lever mechanism.

BACKGROUND OF THE INVENTION

Inhalation into the lungs of a patient of a metered dose of medication is an increasingly common delivery system for a variety of drugs, including but not limited in any way to anti-asthma medications, insulin (See http://www.msnbc.com/news/525058.asp), various steroids and treatments specific to various pulmonary diseases. One concern with metered dose inhalers or aerosol pressurized cartridges has been that, while the metered dose inhaler canister dispenses a fixed, metered dose of medication, not all of the metered dose actually reaches the lungs of the patient. Even if a patient times inhalation with the dispersal of the medication from the metered dose inhaler (MDI), the amount of medication reaching the lungs is inconsistent, depending on how much of the medication is dissolved and entrained in the stream of air entering the patient's lungs, and how much of the medication is deposited on surfaces of the inhalation apparatus, the mouth and oropharyngeal area of the patient. Furthermore, deposits in the mouth and oropharyngeal area of the patient can cause complications, such as candidiasis, as well as leave an unpleasant aftertaste. In addition, many patients using inhalation devices have practical problems with the use of typical inhalers, including difficulty with compressing the metered dose inhaler canister, problems timing inhalation with the dispersal of medication, and inability to inhale the complete dose of medication in a single breath, particularly young, elderly, or patients who suffer from asthma and dysphonia or thrush from inhaled corticosteroids. In practice, it is common to see patients activating their metered dose inhalers multiple times, although the metered dose should have been dispensed in a single activation. This is a typical response of patients to the difficulty and inconsistency of medication delivery, undermining the effectiveness of the MDI, which can lead to over-medication, under-medication, or waste and higher than necessary costs for treatment.

The typical solution to the problem of inconsistent medication delivery has been to provide a "spacer" or "chamber" within the inhalation device. A spacer or chamber is merely a reservoir of air. The metered dose of medication, usually an atomized mist or vapor, mixes with the reservoir of air before being inhaled by the patient, reducing the inconsistency of delivery due to timing difficulties. See U.S. Pat. Nos. 4,470,412; 4,790,305; 4,926,852; 5,012,803; 5,040,527; 5,042,467; 5,816,240; and 6,026,807. An additional improvement incorporated into many of the devices with spacers has been a simple valve mechanism to allow the patient to inhale the medication in more than one breath. For example, see U.S. Pat Nos. 4,470,412; 5,385,140. The efficacy of such devices for correcting errors in patient technique has been shown in general medical research. For example, see Demirkan, et al., "Salmeterol Administration by Metered-Dose Inhaler Alone vs. Metered-Dose Inhaler Plus Valved Holding Chamber," Chest, 117 (2000) pp. 1314–1318, Finlay and Zuberbuhler, "In vitro comparison of beclomethasone and salbutamol metered-dose inhaler aerosols inhaled during pediatric tidal breathing from four valved holding chambers," Chest, 114 (1998) pp. 1676–1680, and Konig, "Spacer devices used with metered-dose inhalers. Breakthrough or gimmick?" Chest, 88 (1985) pp. 276–284.

One problem not generally addressed is the ease of compression of MDI canisters. One spacer, called the EZ Spacer®, http://www.weez.com, improves the ease of compression by allowing the patient or another to use both thumbs on a pull handle and the forefingers on the MDI canister, but this is only a marginal improvement over the standard design, allowing merely one thumb and forefinger for compression of the MDI, and is no aid to patients who do not have full use of both of their thumbs and forefingers.

For infants or other patients who have difficulty using a mouthpiece, a mask is commonly attached or incorporated onto the MDI inhaler. See U.S. Pat. Nos. 4,809,692; 4,832,015; 5,012,804; 5,427,089; 5,645,049; 5,988,160. Also, some devices include an audible signaling device to warn patients when inhalation exceeds a desirable rate. For example, see U.S. Pat. Nos. 4,809,692 and 5,042,467.

One method of attaching a spacer to the MDI canister is to insert the MDI inhaler into a universal adapter such as shown in U.S. Pat. No. 5,848,588, but this is bulky and awkward to use, and does nothing to ease the difficulty of compressing the MDI canister for infirm or ailing patients. Other devices are designed to have a specific MDI canister inserted into the device. It would be beneficial to be able to insert MDI canisters for various medications into an inhaler with a universal receptor.

SUMMARY OF THE INVENTION

The present invention is directed to an inhaler that has universal receptors for at least one medication canister 10 or metered dose inhaler (MDI) canister, also referred to as a cartridge. By the term inhaler, the inventors mean that the device accepts a canister directly into the device, replacing the typical inhaler with an improved inhaler that comprises a receptor for an MDI canister, a spacer, an easy to operate lever arm, and a mouthpiece. One typical embodiment of the invention accepts a single canister, and has a lever arm 22 that is easy to depress, a chamber 210 that acts as a spacer (for example see FIGS. 9, 10 and 12), having an optional valve mechanism (for example see FIG. 11). In one embodiment, the optional valve mechanism is integrally molded with the chamber body and includes at least one inhalation vent 218 (for example see FIG. 12), a diaphragm valve 214, and an optional over-pressure whistle 212, which can be included to improve the efficiency of medication delivery by alerting the patient to improper inhalation technique. In another embodiment, the optional valve mechanism is fabricated separately from the chamber body, and the optional valve mechanism is then fixed to the chamber body. Examples of fixation include but are not limited to adhering, fastening, and inserting of the valve mechanism to the chamber body.

In one preferred embodiment of the mouthpiece, for example see FIG. 10, the mouthpiece 220 is comprised of a flexible, elastic material, and fits tightly around the chamber body 210 at the mouthpiece mating end 211. In one particular embodiment, an annular diaphragm valve 214 is positioned on a retaining member 215 in an optional valve mechanism within the chamber body. During inhalation, the diaphragm valve opens, allowing a mixture of air and medication to flow through at least one inhalation vent 218, then through the mouthpiece 220 and into the patient's lungs. During exhalation, the diaphragm valve 220 closes, keeping the exhaled air from reentering the chamber body. Then, the exhaled air exerts an outward hydrostatic pressure against the sides of the mouthpiece 220. The hydrostatic pressure causes the exhaled air to escape by forcing the air between the mouthpiece 220 and the chamber body 210 at the mouthpiece mating end 211. In one particular embodiment, the mouthpiece mating end 211 has at least one exhaust port 216. In one particular embodiment the exhaust port 216 is a rectangular notch in the side of the mouthpiece mating end 216 of the chamber body 210, wherein the exhaust port 216 is covered by the flexible, elastic material of the mouthpiece 220. In this particular embodiment, the exhaled air preferentially exits through the exhaust port 216, because the flexible, elastic material of the mouthpiece 220 preferentially deflects at the location of the exhaust port 216. In another embodiment, as shown in FIG. 11, the mouthpiece 220 has an exhaust flap 223 or plurality of exhaust flaps defined by slits 224 in the flexible elastic material of the mouthpiece 220, such that the exhaust port 216 or plurality of exhaust ports are covered by the flexible, elastic material of the exhaust flap 223 or plurality of exhaust flaps 220.

In a typical embodiment, the flexible, elastic material fits tightly around the chamber body, sealing the exhaust ports, until the hydrostatic pressure during exhalation becomes great enough to cause exhaled air to be forced between the chamber body and the flexible, elastic material of the mouthpiece. It is preferred that the flexible, elastic material thickness be selected to require at least some minimal exhalation pressure before air escapes between the mouthpiece and the chamber body.

One preferred embodiment of the mouthpiece is comprised of silicone rubber. In addition, other flexible, elastic materials can be used including, but not limited to, butyl rubber, neoprene rubber and latex. The parameters important in the selection of the flexible, elastic material to be used include both the composition and the thickness of the flexible, elastic material. The material should be durable and have sufficient elastic tensile strength to be useful, including resisting normal wear and tear and also holding firmly onto the chamber body when stretched around the outer surface of the chamber body. Furthermore, if the flexible, elastic material is used for the portion of the mouthpiece that the patient inserts into his or her mouth, then the material should be rigid enough to allow the patient to form a tight seal around the mouthpiece during inhalation and exhalation. Alternatively, a rigid insert could be placed within the portion of the mouthpiece that the patient inserts within his or her mouth, and the rigid insert in combination with the flexible, elastic material could be rigid enough to allow the patient to form a tight seal around the mouthpiece during inhalation and exhalation. In yet another embodiment, the rigid insert could extend within the flexible, elastic material completely, except for the flexible, elastic material covering the exhalation ports. In this particular embodiment, the rigid insert could be, for example, could make no contact with the chamber body, could contact the chamber body without fixation, or could be fixed to the chamber body.

In a preferred embodiment, the flexible, elastic material is flexible enough to allow the exhaled air to escape between the mouthpiece and the chamber body at a useful exhalation pressure. The exhalation pressure is greater than zero pounds per square inch (psi) or zero inches of water above the ambient pressure, but the exhalation pressure can be very low, and should be designed to be practical for use by patients with breathing difficulties. By a very low exhaust pressure, the inventors mean that the exhaust pressure is greater than zero and just sufficient to cause exhaust air to exit the mouthpiece between the flexible, elastic material and the chamber body at an exhaust port. The exhaust port can be located very near to the edge of the flexible, elastic material. One typical embodiment had an exhaust pressure less than 2 inches of water above the ambient pressure, but this is not an absolute limit. Indeed, selection of materials, thickness, the presence of exhaust tabs and exhaust tab attachment and exhaust port size and location would allow any practical exhaust pressure to be chosen. Practical minimum and maximum inhalation and exhalation pressures are known in the art or can be determined readily from the preferences of specific drug manufacturers.

When very low exhalation pressure is desirable, it may be beneficial to have a raised lip on the end of the chamber body engaging the mouthpiece. Then, the flexible, elastic material can be made thinner and can be stretched over the lip, helping to retain the mouthpiece on the chamber body. In one particular embodiment of the invention, the exhaust port in the chamber body does not interrupt the lip which extends completely around the chamber body. In this particular embodiment, the mouthpiece is designed to stretch over the lip, and the edge of the mouthpiece is shaped to fit the chamber body. In a preferred embodiment, a retaining ring is used to couple the mouthpiece onto the chamber body. For example, the retaining ring can be positioned over the flexible, elastic material of the mouthpiece where it engages the chamber body, such that the retaining ring couples the mouthpiece and chamber body, more securely fixing the mouthpiece to the chamber body than would be possible by merely relying on the elasticity of the mouthpiece to hold itself on the chamber body. The position of the retaining ring must not interfere with the functioning of the exhaust ports. In one embodiment, this is accomplished by extending the flexible, elastic material of the mouthpiece beyond the retaining ring, such that the flexible, elastic material is free to deform, functioning as an exhaust flap over the exhaust vent. In one embodiment, the edge of the mouthpiece extends at least 0.01 inches beyond the end of the exhaust vent in the chamber body, whereby the exhaust vent is completely covered by the flexible, elastic material of the mouthpiece. In one preferred embodiment, the edge of the mouthpiece extends at least 0.125 inches beyond the end of the exhaust vent. In an alternative embodiment, an exhaust tab is defined by the absence of flexible, elastic material surrounding the exhaust tab, which exhaust tab covers an exhaust port and both the exhaust tab and exhaust port are located between the retaining ring near the end to the mouthpiece and the end of the chamber body on the mouthpiece mating end of the chamber body, such that the retaining ring does not interfere with the functioning of the exhaust port. In this alternative embodiment, the exhaust flap is integrally fixed to the rest of the mouthpiece, but is defined by the removal of flexible, elastic material on one or more sides of the exhaust tab. For example, a square tab can be defined by removal of material on three sides of a square of material, while leaving one side of the square attached to the rest of the flexible, elastic material. It should be clear to one of ordinary skill in the art, that the tab can be defined by any absence of material, even if on only one side, because the flexible, elastic material can expand outward under the exhalation pressure of the patient, allowing air to escape from between the exhaust port and the tab. Therefore, the tab need not be a flap, but can be a mere hole in the flexible, elastic material. In a preferred embodiment of this alternative embodiment, the tab is defined by an absence of flexible, elastic material, except for a connection on one side of the tab that connects the exhaust tab to the rest of the flexible, elastic mouthpiece.

Alternatively, the chamber body could have a depression in the surface. For example, the depression could be a groove around the chamber body at the mouthpiece mating end of the chamber body. Then, a raised rib around the inside of the flexible, elastic material of the mouthpiece could engage the depression in the surface of the chamber body, interlocking the mouthpiece and the chamber body. The groove in the chamber body and raised rib on the mouthpiece could act to secure the mouthpiece onto the chamber body, allowing use of a thinner material than would otherwise be practical for securing the mouthpiece to the chamber body. Alternatively, a retaining ring could be used to mate with the depression in the chamber body, coupling the mouthpiece to the chamber body.

In another alternative embodiment, a structured exhaust valve can be used that comprises an exhaust port and additional structure. A "structured exhaust valve" is used to describe an exhaust valve that is more than merely an exhaust port in the surface of the chamber body, directing the exhaled air through an exhaust vent, which directs the exhaled air, for example, to a limited region near the end of the exhaust flap defined by slits in the flexible, elastic material.

In addition, a flexible, elastic material that is both inert to the contents of the MDI and nontoxic to the patient is preferred. By inert, the inventors mean that the flexible, elastic material avoids any substantial chemical reactivity with the contents of the MDI. Substantial chemical reactivity is defined functionally, such that a substantial chemical reaction is one that causes a severe degradation of the mouthpiece. Such chemical reactions and compatibilities of flexible, elastic materials with medications used in inhalers are known in the art.

A severe degradation of the mouthpiece renders the mouthpiece unusable including, but not limited thereto, to causing an unhealthy or toxic contamination of the mouthpiece or medication passing through the mouthpiece, or causing a failure of the mouthpiece to function, for example impeding flow of air through an exhalation vent, allowing air to leak into the exhaust port during inhalation, or sticking an exhaust flap to the surface of the chamber body. Severe degradation can be caused by embrittling, tackifying, or softening of the flexible, elastic material. By tackifying, the inventors mean that the flexible, elastic material undergoes a chemical reaction that causes the surface of the flexible, elastic material to become "tacky," which means that the surface becomes sticky to the surface of the chamber body. Embrittling causes the material to become rigid impeding flow of air or to crack allowing inhaled air to enter through an exhaust port. Softening causes the material to lose its rigidity and tensile strength, losing its shape or its ability to grip the chamber body with sufficient force to remain in place on the chamber body.

Tests for chemical reactivity are notoriously well known to one of ordinary skill in the art. Tests can be performed to determine if a specific material is chemically inert to a specific medication or to an array of medications. In one method of testing, samples of the material can be exposed to one or more medications and changes in the physical or chemical properties of the material can be measured to determine compatibility. For example, chemical reactivity can be revealed by endothermic or exothermic heat transfer following contact of a material with a specific medication. Also, changes in color of a material, changes in the composition of a material, and changes in the weight, volume or other physical properties of a material can be observed as indicators of chemical incompatibility. One of ordinary skill in the art should be familiar with the techniques required to assess chemical compatibility between a material and a medication.

In addition, one possible embodiment could use additives in the flexible, elastic material or coatings on the surface of the flexible, elastic material to arrest or reduce to acceptable levels any undesirable chemical reaction between a material and a medication.

Another typical embodiment of the invention accepts two canisters (dual canisters), and has a lever arm 22 that is easy to depress, a chamber 24 that acts as a spacer, and a mouthpiece 25, having an optional valve mechanism 62 and over-pressure whistle 63, that improves the efficiency of medication delivery, and a slidable selector switch 21 that permits the user to select the mode of operation. The modes of operation include selecting either of the two canisters individually. An additional non-operational setting locks the actuator lever 23 to prevent inadvertent dispensing of medication during periods of non-use.

One object of the invention benefits patients who are infirm or young, by reducing the difficulty in using an inhalation device. The actuator lever 23 allows the entire hand to be used in depressing the MDI canister, and also provides a mechanical advantage, reducing the pressure necessary to dispense the medication. The sliding selector switch 21, for example of a dual canister embodiment, is easy to manipulate, and can be put into position to operate either of the dual canisters individually with one hand. The optional locking position can also be selected by a patient with only one hand. An optional indicator shows which of the two canisters is selected by the sliding selector switch.

In a preferred embodiment of the multi-canister inhaler, the dual canister design allows two different kinds of medication to be dispensed by a single inhaler. Increasingly, patients require multiple MDI medications, and the use of a single inhaler for two different medications, which reside conveniently within the inhaler, reduces problems with storage, retrieval, and insertion of MDI canisters into the inhaler for those that are infirm, young or in distress. Alternatively, the second canister may be inserted as a reserve supply for those patients that require assistance with insertion of canisters into an inhalation device, allowing the patient to switch to the reserve supply by merely pushing the sliding selector switch.

In one embodiment, the standard, universal cowling is designed to accept MDI canisters of nearly all commonly prescribed medications, and the cowling helps to guide the canister into the inlet port of the housing when the patient inserts a MDI canister into the inhaler. In addition, the cowling provides support to the canister when the patient depresses the actuator lever, dispensing medication into the housing of the inhaler. Specialized cowlings may be designed for unusual MDI canisters or new MDI canisters that would not fit the universal cowling. By universal, the inventors mean that the cowling is designed to accept nearly all commonly prescribed MDI canisters.

Upon dispensing the medication, the atomized mist from the inhaler is directed through the housing and into the chamber. During inhalation by the patient in one typical embodiment of the invention, a vent in the housing brings fresh air into the housing sweeping the remaining atomized mist from the housing into the chamber, where it mixes with the air, and is drawn into the patients lungs through the patients mouth. In one preferred embodiment of the invention a valve assembly in the mouthpiece of the chamber allows the mixture of medication and air to be drawn through the mouthpiece during inhalation, see FIG. 8, for example, but during exhalation, the inhalation valve closes, and an exhalation valve opens, allowing the exhaled air to escape from an exhalation vent in the mouthpiece. This allows the patient to inhale the medication in multiple breaths.

It should be obvious to one of ordinary skill in the art that an inhaler with access ports for more than two canisters could be configured in the same way as the dual canister design shown in the figures, and presented in the detailed description of the invention. Indeed, the invention is not limited to a dual canister design, but would include a multiple canister design, which includes a sliding selector switch able to engage each of the multiple MDI canisters inserted into an expanded cowling.

BRIEF DESCRIPTION OF THE FIGURES

For the purpose of illustrating the invention, representative embodiments are shown in the accompanying figures, it being understood that the invention is not intended to be limited to the precise arrangements and instrumentalities shown.

DETAILED DESCRIPTION OF THE PREFERRED EMBODIMENTS

The present invention will now be described in detail for specific preferred embodiments of the invention. These embodiments are intended only as illustrative examples and the invention is not to be limited thereto.

Figure 5:
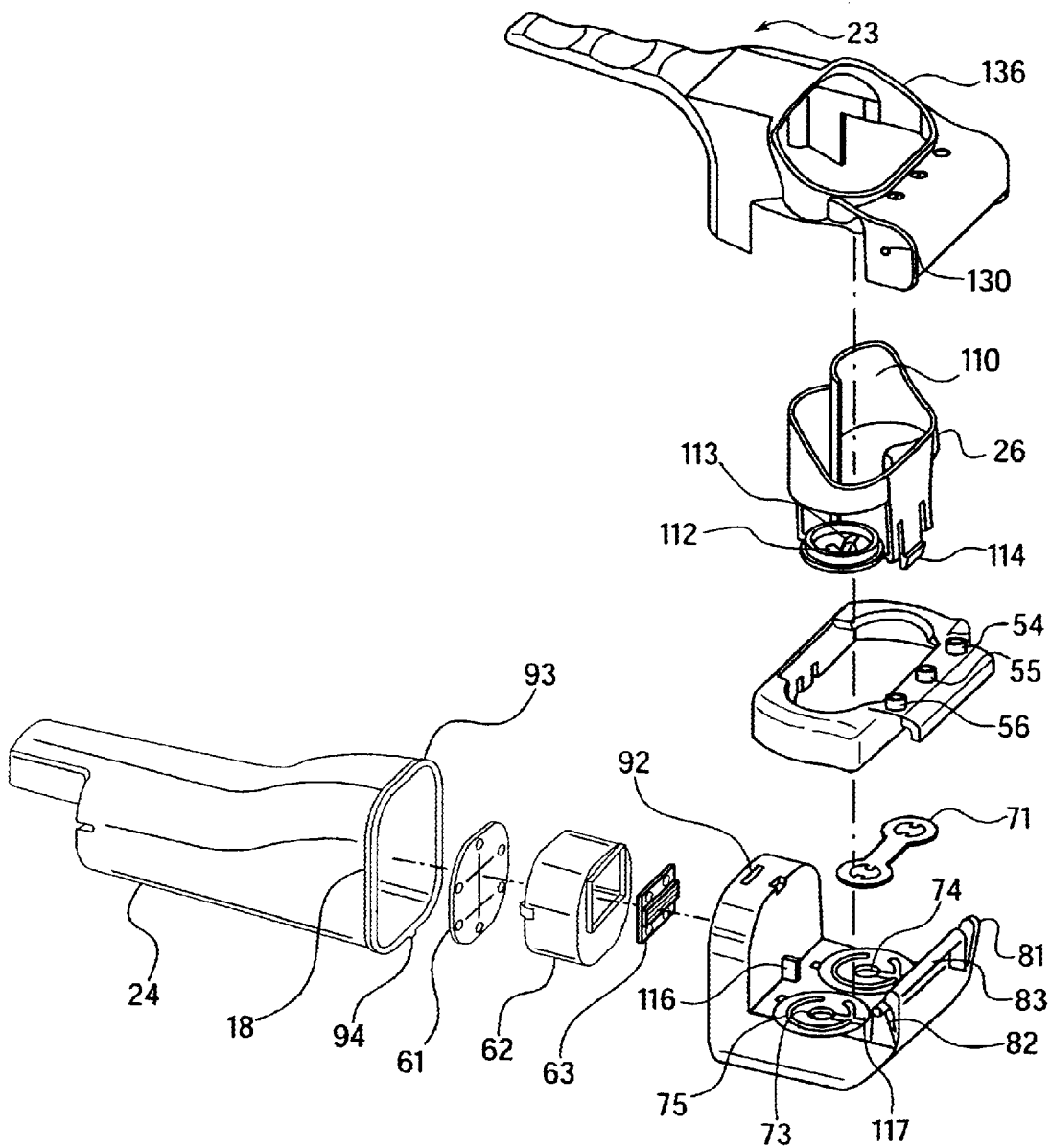
FIG. 5 shows a perspective, exploded view of one typical embodiment of the invention, including the chamber, valve, valve body, whistle, housing, canister locking mechanism, sliding selector switch, cowling, and actuator lever.

One embodiment of the present invention is an inhaler for delivery of medication from either of a first canister 10 or a second canister 11 to the lungs of a patient by inhalation through the patient's mouth. The first and second canisters are not a part of the invention, but are supplied by pharmaceutical companies. This embodiment of the invention accepts nearly all of the commonly prescribed MDI canisters, which have a compression spray outlet. The inhaler comprises a cowling 26, which is a universal receptor and holder for the MDI canisters. In a typical embodiment, a dual canister inhaler has a cowling, which is further comprised of a support structure 110, a first canister receptor and a second canister receptor. Each of the first canister receptor and the second canister receptor has a flexible fitting 113 and a ring 114. The flexible fitting is supported within the ring. The ring has an inner diameter, which supports and guides the compression spray outlets of each of the MDI canisters into the flexible fitting. The flexible fitting engages the compression spray outlet 14 (See FIG. 8) of each of the two canisters, creating a seal around compression spray outlets of the MDI canisters. The support structure of the cowling 26 has the ring and flexible fitting fixed in one end, and the other end is open, allowing the patient to insert each of the two MDI canisters into the cowling. The shape of the inner walls of the support structure 110 of the cowling is the same cylindrical shape typical of MDI canisters, but the wall of the support structure is not homogeneously solid. As shown in FIG. 5, one embodiment of the cowling has solid cylindrical walls only on the upper half of the cowling. The solid wall in the upper half of the cowling helps the patient insert the MDI canister into the inhaler. The lower half has solid walls connecting to the ring only on the front and back surfaces of the cowling. This allows a sliding selector switch to engage the lip of a MDI canister to selectively engage either one or the other MDI canister that is inserted into the cowling.

In another embodiment, the support structure of the cowling could have solid walls on the left and right of the cowling, connecting to the ring, allowing a sliding selector switch to engage the lip of a MDI canister from the front and back of the cowling. It would be obvious to one skilled in the art that other combinations are possible for allowing the sliding selector switch to engage an MDI canister in the cowling, and these alternatives are included within the scope of this invention.

Figure 8:
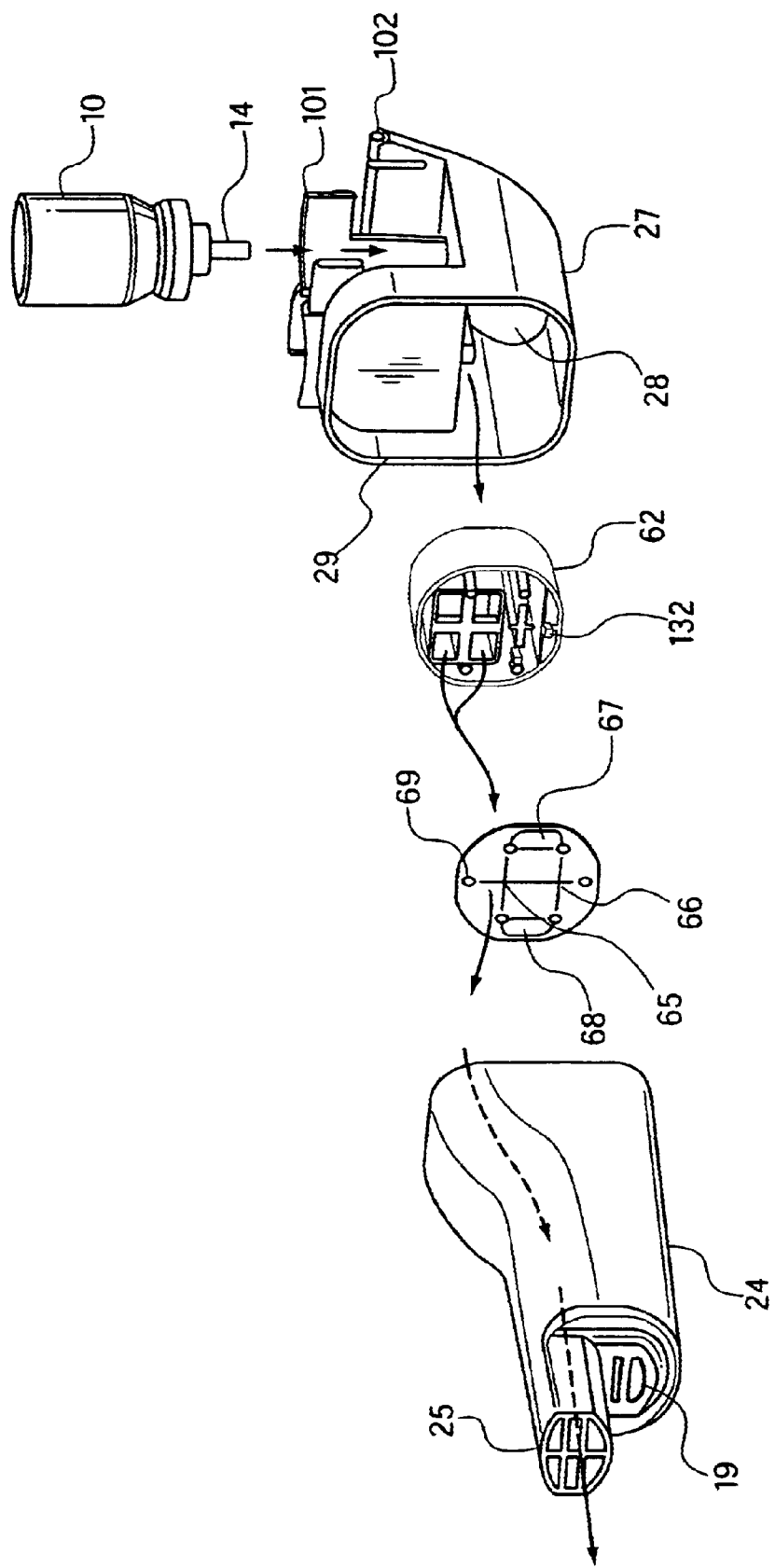
FIG. 8 shows a perspective, exploded view of a portion of one typical embodiment of the invention, including a housing, a valve body, a diaphragm valve, and the chamber body, and the path of air occurring during inhalation by the patient.

In yet another embodiment, the support structure of the cowling 101 is solid on the front and back, and their is a connecting solid between the structure supporting the two canisters, as shown in FIG. 8. In this embodiment, the exterior sides are left open. The particular embodiment shown in FIG. 8 also shows an alternative embodiment for the flexible fitting and ring. In this particular embodiment, the ring and flexible fitting were omitted intentionally, and the compression spray outlet entered directly into the cowling receiving section inlet port of the housing. A preferred embodiment of the cowling receiving section is described in detail below.

The cowling of this invention acts to hold the canisters in place, also. In an alternative embodiment, a locking plate 71 is included that mechanically locks each of the MDI canisters in place within the cowling 26. FIG. 5 shows an example of a locking plate.

Figure 6:
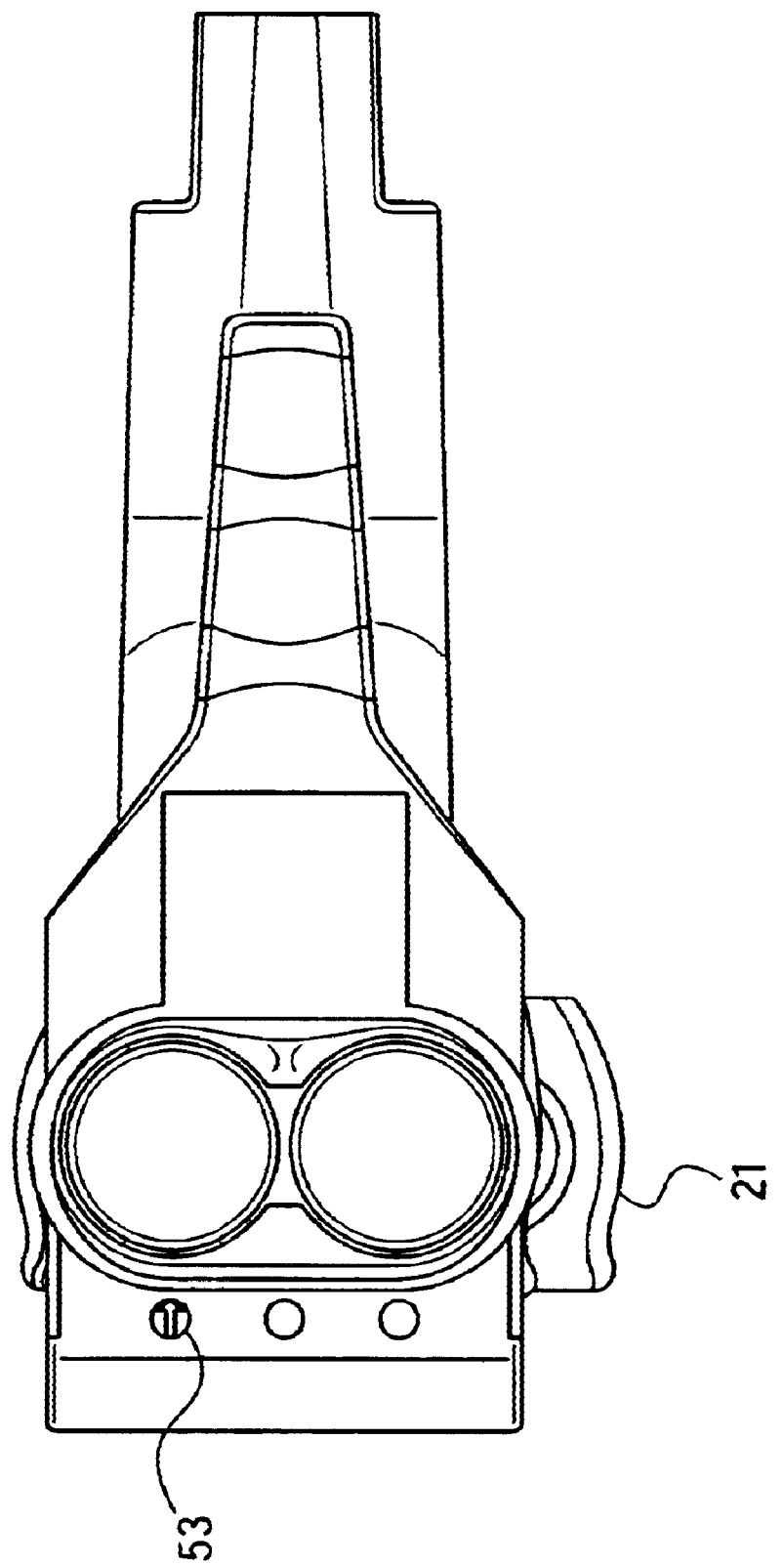
FIG. 6 shows a top view of one typical embodiment of the invention, further showing the sliding selector switch in the first position for engaging the first canister.
Figure 7:
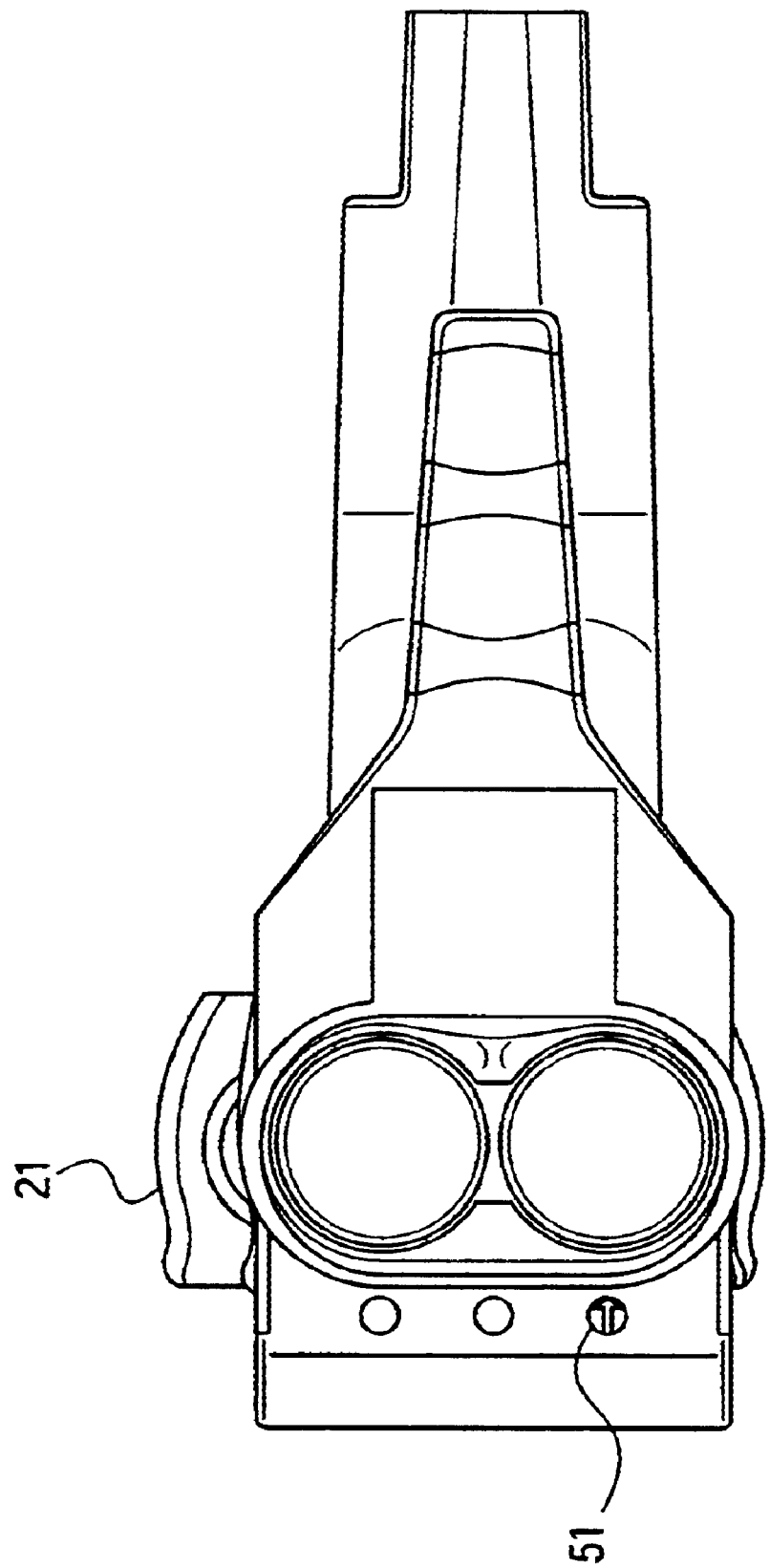
FIG. 7 shows a top view of one typical embodiment of the invention, further showing the sliding selector switch in the second position for engaging the second canister.

The previously mentioned sliding selector switch 21 has the same number of operating positions as there are canisters. Therefore, a dual canister design has both a first operating position, see FIG. 6, and a second operating position, See FIG. 7. By operating position, the inventors mean that one of the canisters is engaged by the sliding selector switch (or selector), and by depressing an actuator lever, the canister can be activated by the patient, dispensing medication. An example of an indicator display mechanism is illustrated in FIGS. 6 and 7. When the selector is in the first operating position, a first arrow 56 is visible in the first indicator window 53 and points to the first canister 10. When the selector is in the second operating position, as second arrow 54 is visible in the second indicator window 51 and points to the second canister 11.

In an alternative embodiment, the sliding selector switch 21 has a non-operative, locking position, which keeps an actuator lever 23 from being depressed by locking the actuating lever in the fully depressed position. In an alternative embodiment, the locking mechanism can lock the actuator lever in the fully deployed or up position. In yet another alternative, the locking mechanism is simply moved to a non-functional position, which engages no MDI canister; therefore, the actuator lever freely moves without engaging any canister, and this embodiment can also incorporate a means for securing the actuator lever in the fully depressed or down position. This means for securing can be a fastener, an elastic band, a twist, a hold down, a hook, a snap, a keeper mounted on the chamber body or a detent on the chamber body that engages a protrusion attached to the bottom of the lever arm that approximates the shape of a portion of an oblate spheroid. In a preferred embodiment, the lever arm would be prevented from engaging the means for securing when in an operating position, because the lever arm would never be completely depressed unless the sliding selector switch was placed in the non-operating, locking position. Then, the patient could simply snap the lever arm into the locked position.

In one embodiment the cowling 26 is a part of a larger housing assembly. Alternatively, the cowling is mechanically engaged, fastened, attached, fixed, fused or adhered within a cowling receiving section of the housing or a housing assembly of the inhaler. In general, the inventor refers to these various methods of incorporating the cowling within the cowling receiving section by the term fixedly seated; therefore, the cowling is fixedly seated within the cowling receiving section.

In one embodiment of the invention, the housing comprises a chamber receiving section 29, a cowling receiving section, a sliding selector switch support 83, a fresh air inlet 75, and an enclosed passage. In this embodiment the cowling receiving section is shaped to accept the shape of the outer dimensions of the cowling 26, and the sliding selector switch 21. As one example, the cowling can be fixedly seated in the cowling receiving section, as shown in FIG. 5, using an integral securing tab 114. The cowling receiving section in FIG. 5 has an upright centered tab support 116 and two upright pin supports, for example item 117, that seat the cowling 26 within the cowling receiving section. Other ways of fixedly seating the cowling in the cowling receiving section of the housing are known in the art and are within the scope of this invention, and the invention is not limited to the description in this particular example.

The cowling receiving section has cowling receiving section inlet ports, corresponding to the position and number of MDI canisters that the cowling accepts. For a dual canister inhaler, two receiving section inlet ports 73,74 are located in the housing. When the MDI canisters are inserted into the cowling by the patient, the MDI canister compression spray outlets are inserted into the flexible fittings of the cowling. Thereby, each of the compression spray outlets extends into the cowling receiving section inlet ports of the housing and into the enclosed passage of the housing.

The enclosed passage of the housing is defined by the inner surface of the housing (interior walls). The enclosed passage of the housing ends in the chamber receiving section. An example of the chamber receiving section 29 is the opening of the housing adjacent to the chamber, as shown in FIG. 8. In one embodiment of the invention, the interior surface of the housing defines a compression spray outlet engaging stage, also. The compression spray outlet engaging stage, in this particular embodiment, is merely a platform in the housing below the cowling receiving section inlet ports, which engages the compression spray outlets of the MDI canisters, when either of the MDI canisters is depressed by the patient, depressing the actuator lever of the inhaler. In one specific embodiment, the compression spray outlet engaging stage is defined by a protrusion of the surface of the housing back into the cavity of the housing. By protrusion, the inventors mean that the solid wall that defines the surface of the housing has an indentation on one end that extends back into the cavity of the housing, making a shelf within the housing that leaves sufficient space for the compression spray outlet to rest on the shelf, when the canister is fully inserted into the cowling. In one embodiment, the shelf gradually slopes downward toward the chamber receiving section; therefore, when the compression spray outlet of the canister is depressed, there is a gap between the shelf and the compression spray outlet. This causes the dispersal of the medication to occur in the general direction of the chamber receiving section. In another embodiment, the shelf is essentially flat, and the spray from the compression spray outlet is randomly dispersed throughout the enclosed passage of the housing. In yet another embodiment of the invention, channels are formed in the compression spray outlet engaging stage, wherein each of the compression spray outlets of the MDI canisters fit into a closed end of one of the channels, and the other end of the channels are open, directing the spray from the compression spray outlet in a desired direction within the housing of the inhaler. For example, in one embodiment, the channel directs the spray in the direction of the chamber, and in another embodiment, the channel directs the spray in a direction opposite to the chamber, enhancing mixing of the spray with external, fresh air entering through an inhalation vent in the housing prior to the spray entering the chamber through the enclosed passage of the housing. A portion of a protrusion that forms a down-sloping compression spray outlet engaging stage of one of the embodiments of the invention is shown in FIG. 8 and is labeled as item 28.

In yet another embodiment, the protrusion is replaced by a compression spray outlet engaging stage that is defined by a step-like feature in the surface of the housing. By a step-like feature, the inventors mean that, instead of a protrusion back into the housing, the housing appears to have a tread and riser of step with a nearly 90-degree angle or more preferably an arcuate transition, which similarly defines a shelf within the housing below the cowling receiving section inlet ports. This shelf performs the same function as the shelf formed by the protrusion, and can likewise slope downward toward the chamber to direct the medications toward the chamber.

In yet other embodiments of the invention, the shelf-like feature of the previous embodiments is replaced by inserts placed between the housing and the cowling. The insert of one alternative embodiment of the invention is essentially a tube with two open ends, having one end that flares to a flange and the other end having a conical shape. The conically-shaped end of the insert is inserted into the housing through the cowling receiving port, and the flared flange end centers the insert within the cowling receiving port and secures the insert in place by fixing it between the housing and the ring in the cowling. One of the inserts is placed in each of the cowling receiving section inlet ports of the housing. When the patient inserts a canister into the cowling, the compression spray outlet of the canister is inserted into the tube of the insert. The length and diameter of the tube of the insert are selected to allow nearly all of the compression spray outlets of commonly prescribed MDI canisters to fit within the tube, with the end of the compression spray outlet resting in the taper of the conical tip of the tube of the insert. Therefore, when the patient depresses the actuator lever 23, the compression spray outlet 14 is compressed, causing dispersal of medication into the enclosed passage of the housing. In another embodiment, the inserts are mechanically attached to the housing. In an alternative embodiment the inserts are fixed to the housing. In yet another embodiment, the structure referred to as an insert is integral to the cowling receiving section inlet ports of the housing. In yet another embodiment, two inserts are joined to each other by a tab of solid between them. Other ways to compress the compression spray outlets of a MDI canister are known in the art and are included within the scope of this invention.

All of the various ways of compressing the spray outlets of the MDI canisters are referred to herein, generally, as a compression spray outlet compression mechanism. The term compression spray outlet engaging device refers solely to an insert device, and the term compression spray outlet engaging stage refers solely to a platform within the housing, which can be an attached platform or an integral compression spray outlet engaging stage. The term integral compression spray outlet engaging stage refers solely to a compression spray outlet engaging stage that is formed by a protrusion or a step-like feature in the surface of the housing, itself.

The sliding selector switch 21 is slidably and pivotally mounted on the sliding selector switch support 83. In a dual canister inhaler, the sliding selector switch is capable of engaging either canister, individually, when positioned by the patient in one of the two corresponding operating positions.

An actuator lever 23 has a lever arm 22 and a distal end 20. The distal end 20 of the actuator lever 23 is pivotally mounted on the sliding selector switch support 83 of the housing and engages the sliding selector switch 21, when the actuator lever 23 is depressed by the patient. The distal end 20 of the actuator lever 23 has a cowling opening 136, wherein the cowling 26 and canisters 10,11 pass through the cowling opening 136. In one embodiment the actuator lever is pivotally mounted to the sliding selector switch support of the housing by a pin. A more preferred embodiment is shown in FIG. 5; the distal end 20 of the actuator lever has a hole on each side 130 that engage two corresponding keepers 81,82 extending from the sliding selector switch support 83 of the housing. Yet another embodiment of the actuator lever pivotal attachment is shown in FIG. 8, which is a mechanism similar to the mechanism in FIG. 5, except that the keeper 102 is integral with the sliding selector switch support, having projecting pins from each end of the sliding selector switch support. Other methods of pivotally attaching the actuator are know in the art and are included within the scope of the invention, and the invention is not to be limited to the examples and description herein.

A chamber further comprises a chamber body, 24 a mouthpiece 25 and an housing mating section 18, wherein the chamber body is a solid shell that connects the mouthpiece at one end of the chamber body to the housing mating section at the opposing end of the chamber body. The housing mating section is an opening in the chamber, and the housing mating section 18 engages the chamber receiving section 29 of the housing 27. In one embodiment, shown in FIG. 5, the open housing mating section 18 fits into the chamber receiving section 29 of the housing 27, a tab on the top of the housing mating section 93 fits a slot in the top of the chamber receiving section 92, and another tab on the bottom of the housing mating section 94 slidably locks into a corresponding slot on the chamber receiving section. In another embodiment the housing mating section fits over the chamber receiving section, and the tabs and slots are reversed, tabs on the chamber receiving section and slots on the housing mating section. Any combination of opposing tabs and slots would suffice for joining the two sections, whether on the tops or sides of the two sections.

By using the term engages, the inventors specifically include known methods of fastening, fusing, adhering and attaching the sections to each other, but do not limit the scope of the invention thereto. Yet other means of mechanically engaging the two sections are known in the art and are included within the scope of the invention.

The mouthpiece 25 is shaped to fit the patient's mouth and has a mouthpiece vent, which allows the mixture of air and medication in the chamber body to enter the patient's mouth flow to the patient's lungs, during inhalation. An example is shown in FIG. 8. In an alternative embodiment, a face mask can be attached to end of the mouthpiece. Face masks are known in the art and are designed to conform to the patient's face for patients that cannot use the mouthpiece properly. Then inventors use the term mouthpiece to refer to the portion of the chamber that includes the surface structure of the mouthpiece, the mouthpiece vent and, in alternative embodiments of the invention, the exhalation vent or exhalation port and the valve assembly fixed within the mouthpiece end of the chamber body.

Figure 1:
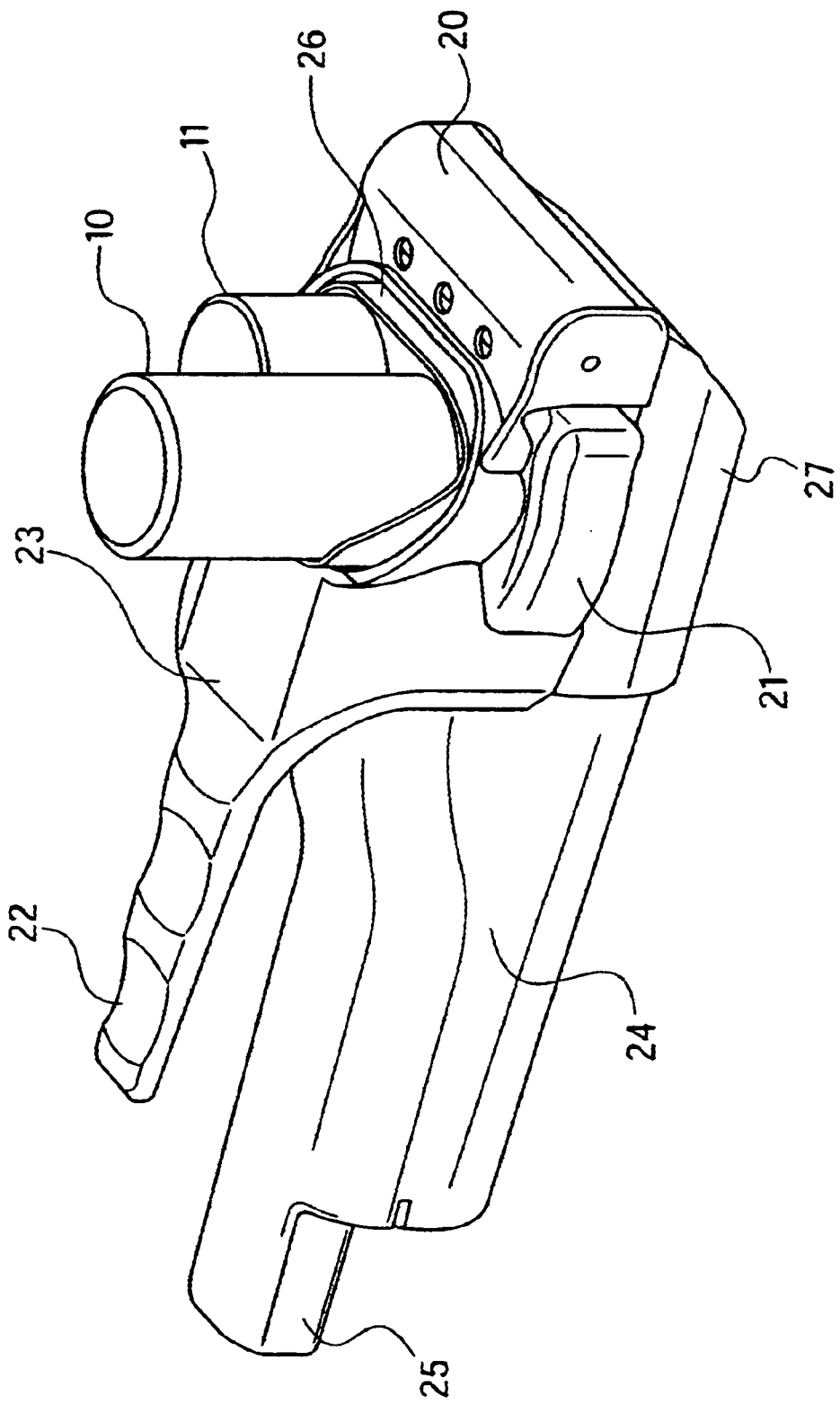
FIG. 1 is a perspective view of one typical embodiment of the invention.
Figure 2:
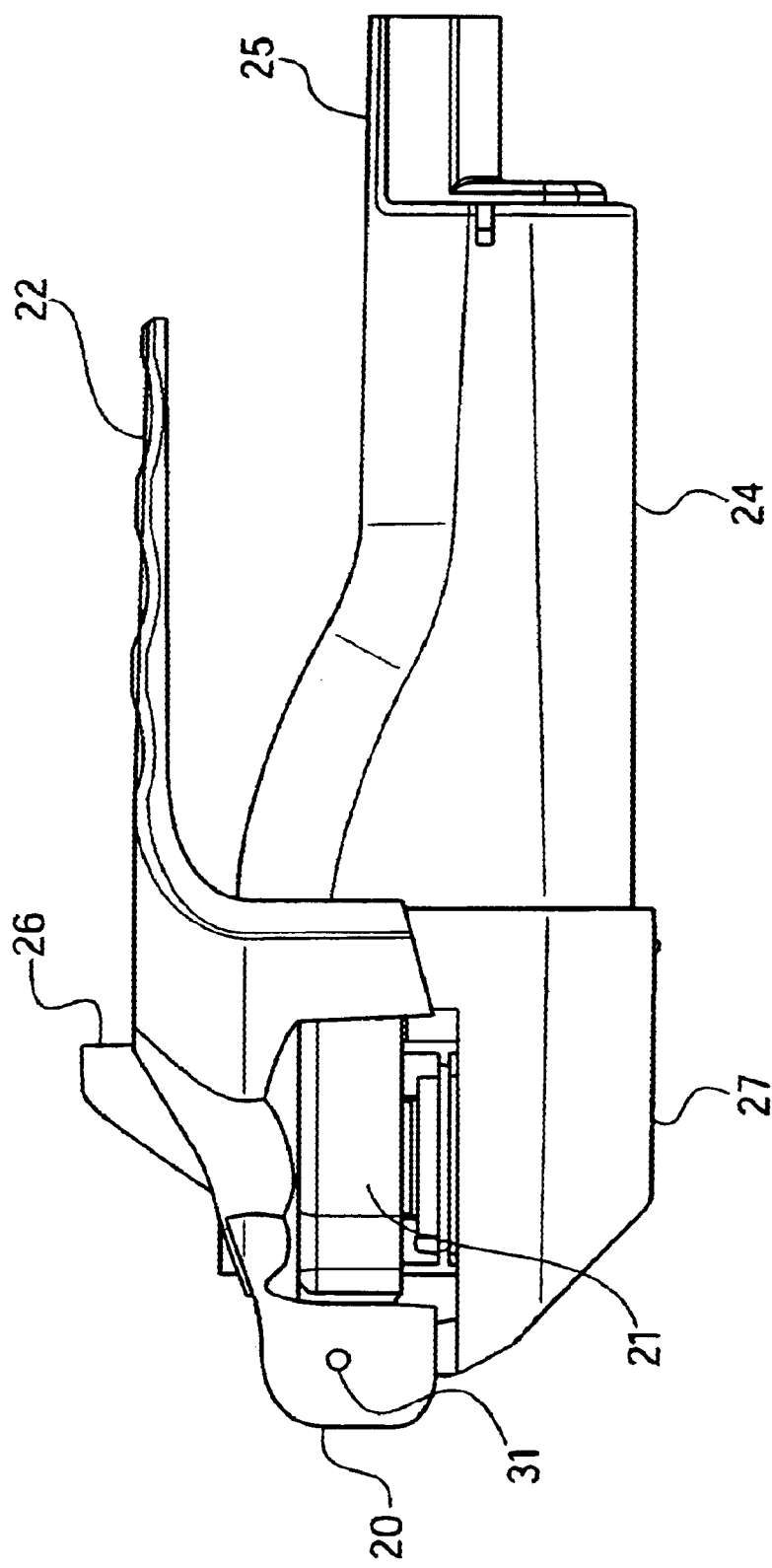
FIG. 2 is a side view of one typical embodiment of the invention, showing a pivotally attached actuator lever engaging the slidable selector switch.
Figure 3:
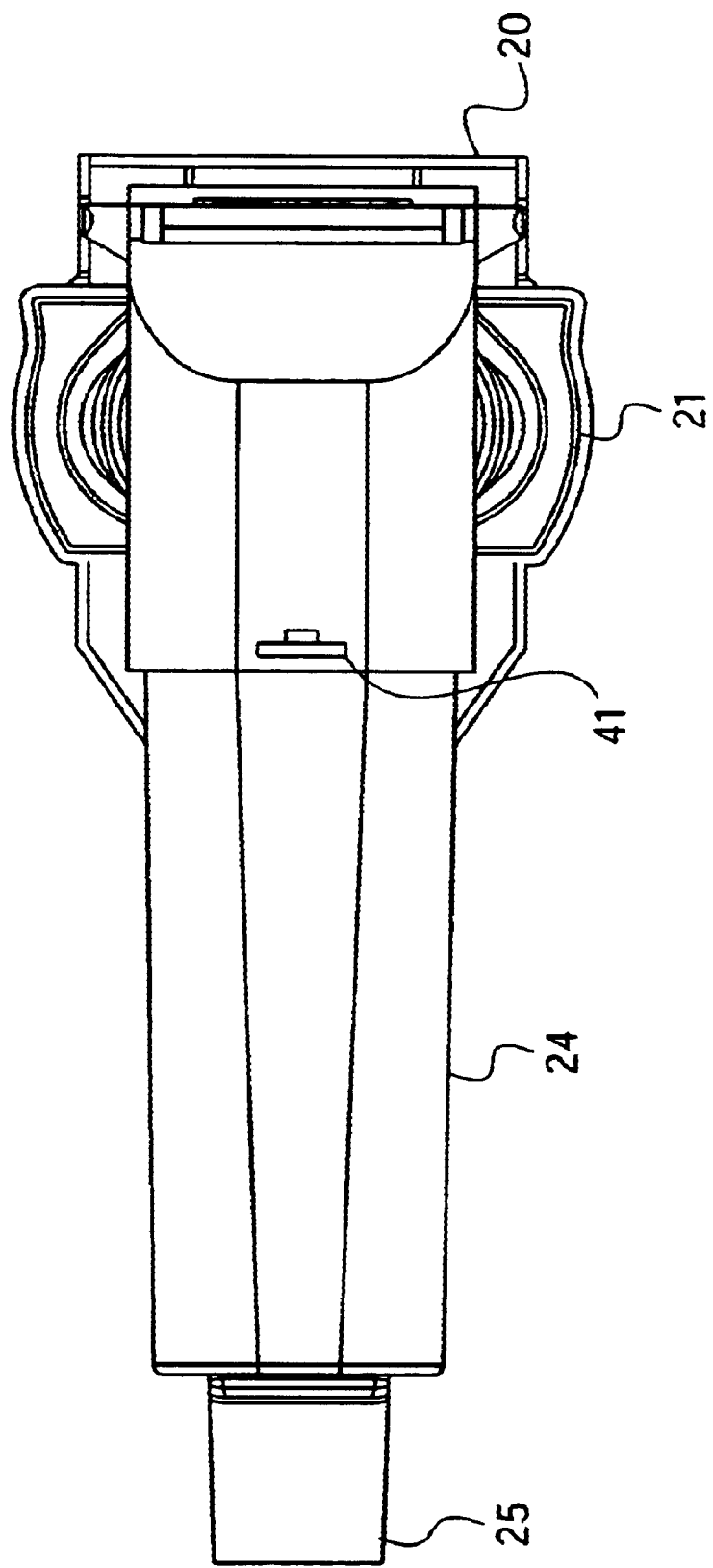
FIG. 3 shows a bottom view of one typical embodiment of the invention, further showing the mechanical attachment release tab.
Figure 4:
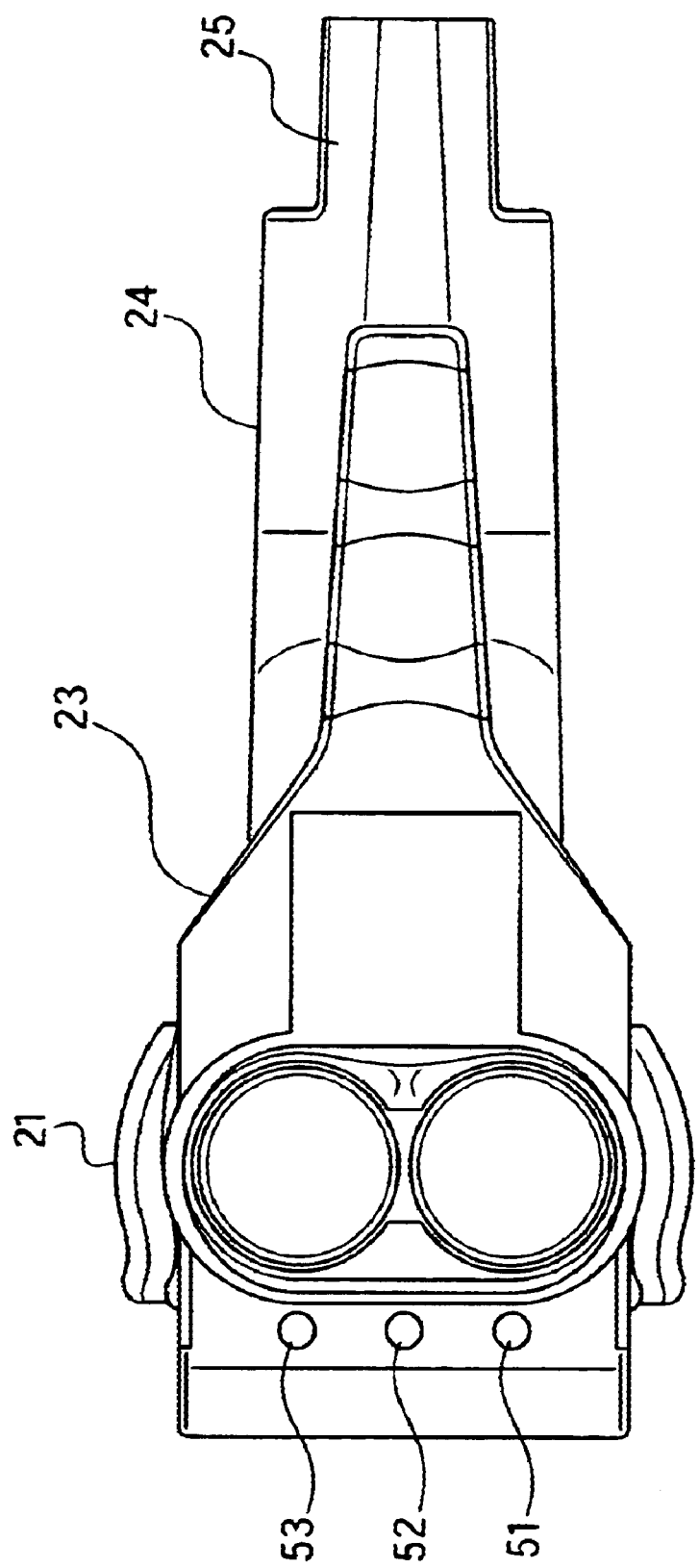
FIG. 4 shows a top view of one typical embodiment of the invention, further showing three indicator windows to indicate the operational position of the sliding selector switch.

As shown in FIG. 2, the chamber 24 opposes the actuator lever 22, and a patient can easily depress the actuator lever by squeezing the lever arm to the chamber body using the patient's entire hand, rather than only the thumb and forefinger. In addition, the actuator lever 24 provides a mechanical advantage, reducing the force that must be applied by the patient to activate an MDI canister. Depressing the actuator lever engages the sliding selector switch 21. If the sliding selector switch 21 is in the first operating position, then the compression spray outlet of the first canister is activated. If the sliding selector switch is in the second operating position, then the compression spray outlet of the second canister is activated. Medication is dispensed from either the first canister or the second canister, respectively.

Upon dispensing the medication, the atomized mist from the inhaler is directed through the housing 27 and into the chamber 24. During inhalation by the patient, a vent in the housing brings fresh air into the housing sweeping the remaining atomized mist from the housing into the chamber, where it mixes with the air, and is drawn through the mouthpiece and into the patient's lungs through the patient's mouth. In one preferred embodiment of the invention, a valve assembly in the mouthpiece of the chamber allows the mixture of medication and air to be drawn through the mouthpiece during inhalation, but during exhalation, the inhalation valve closes, and an exhalation valve opens, allowing the exhaled air to escape from an exhalation vent in the mouthpiece. This allows the patient to inhale the medication in multiple breaths.

One embodiment of a diaphragm valve 61 and valve body 62 are shown in FIGS. 5 and 8. During inhalation air passes through the top cross-slit 65, and the bottom cross-slit 66 is closed against the valve body, keeping any external air from entering the mouthpiece through the exhalation vent 19. During exhalation, the top cross-slit 65 closes against the valve body, and the bottom cross-slit 66 opens, allowing exhaled air to exit through the two oval openings 67,68 on the diaphragm valve. The direction of the air reverses direction within the valve body 62, and exits through the open bottom cross-slit 65 out the exhalation vent 19 of the mouthpiece. In an embodiment without a valve assembly of any kind, there would also be no exhalation vent in the mouthpiece. The mouthpiece can be integral to the chamber, or the mouthpiece can be mechanically attached, fastened, fused or adhesively bonded to the chamber body. In a preferred embodiment, a single diaphragm valve and valve body are fixed in the mouthpiece, and the diaphragm valve is held in position by the rod-like projections (for example item 132 in FIG. 8) from the valve body that engage corresponding holes in projections extending from the mouthpiece and exhalation vent (not shown). The rod-like projections extend through the holes in the periphery of the diaphragm valve (for example item 69 in FIG. 8), and the projections extending from the mouthpiece and exhalation vent force the diaphragm valve 61 to be in direct contact with the valve body 62. In another embodiment of the invention, the inhalation valve is located at the inlet of the housing, while the exhalation valve remains in the mouthpiece. In yet another embodiment of the invention, the inhaler has an inhalation valve located in the mouthpiece, or in an alternative embodiment in the housing, and no exhalation valve is present, requiring the patient to remove the inhaler from the patient's mouth while exhaling or to exhale through the patient's nose.

The return pressure exerted by the MDI canister is sufficient to return the actuator lever 23 to the up position (or deployed position), without any additional spring mechanism. If desirable for ergonomic reasons, it is known in the art how to insert a spring mechanism into the design. For example, a coil spring could be added at the distal end, where the distal end is pivotally attached to the housing, if it were desirable to add some additional resistance to the actuator lever or for any other reason. Addition of a an additional spring mechanism is within the scope of the invention.

The standard, universal cowling is designed to accept MDI canisters of nearly all commonly prescribed medications, and the cowling helps to guide the canister into the inlet port of the housing when the patient inserts a MDI canister into the inhaler. In addition, the cowling provides support to the canister when the patient depresses the actuator lever, dispensing medication into the housing of the inhaler. Specialized cowlings may be designed for unusual MDI canisters or new MDI canisters that would not fit the universal cowling. By universal, the inventors mean that the cowling is designed to accept nearly all commonly prescribed MDI canisters.

An example of an optional audible signaling device or whistle is shown in FIG. 5. The whistle shown is installed in the valve body in the mouthpiece. In an alternative embodiment, the whistle is installed in the inlet of the housing. The term whistle is used here synonymously with any type of audible signaling device that can be made to impart an audible warning when the rate of air, or alternatively the air over-pressure, exceeds a desirable limit during inhalation. The purpose of the whistle is to alert the patient that the patient is inhaling too rapidly, allowing the patient to reduce the rate of inhalation, improving the efficacy of delivery.

Figure 9:
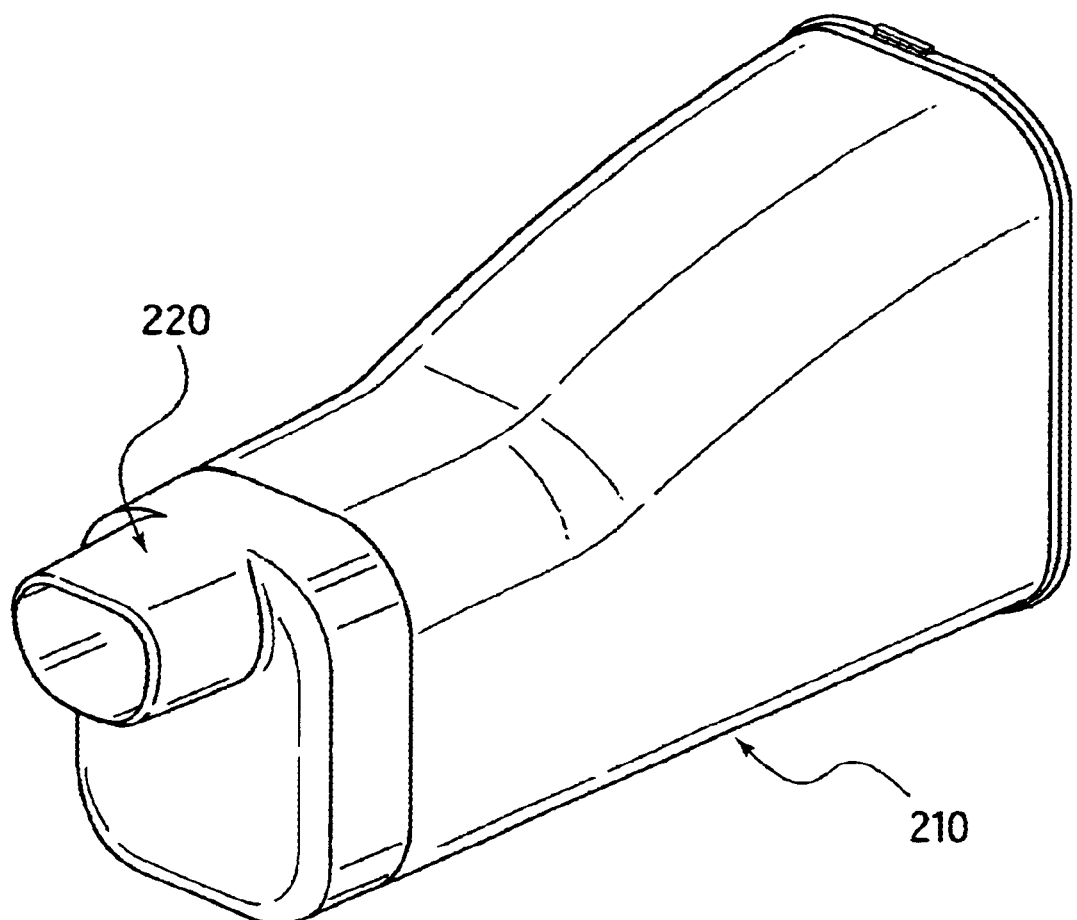
FIG. 9 shows an exterior perspective view of one embodiment of a mouthpiece comprising a flexible, elastic material engaged onto the chamber body of the canister inhaler.
Figure 10:
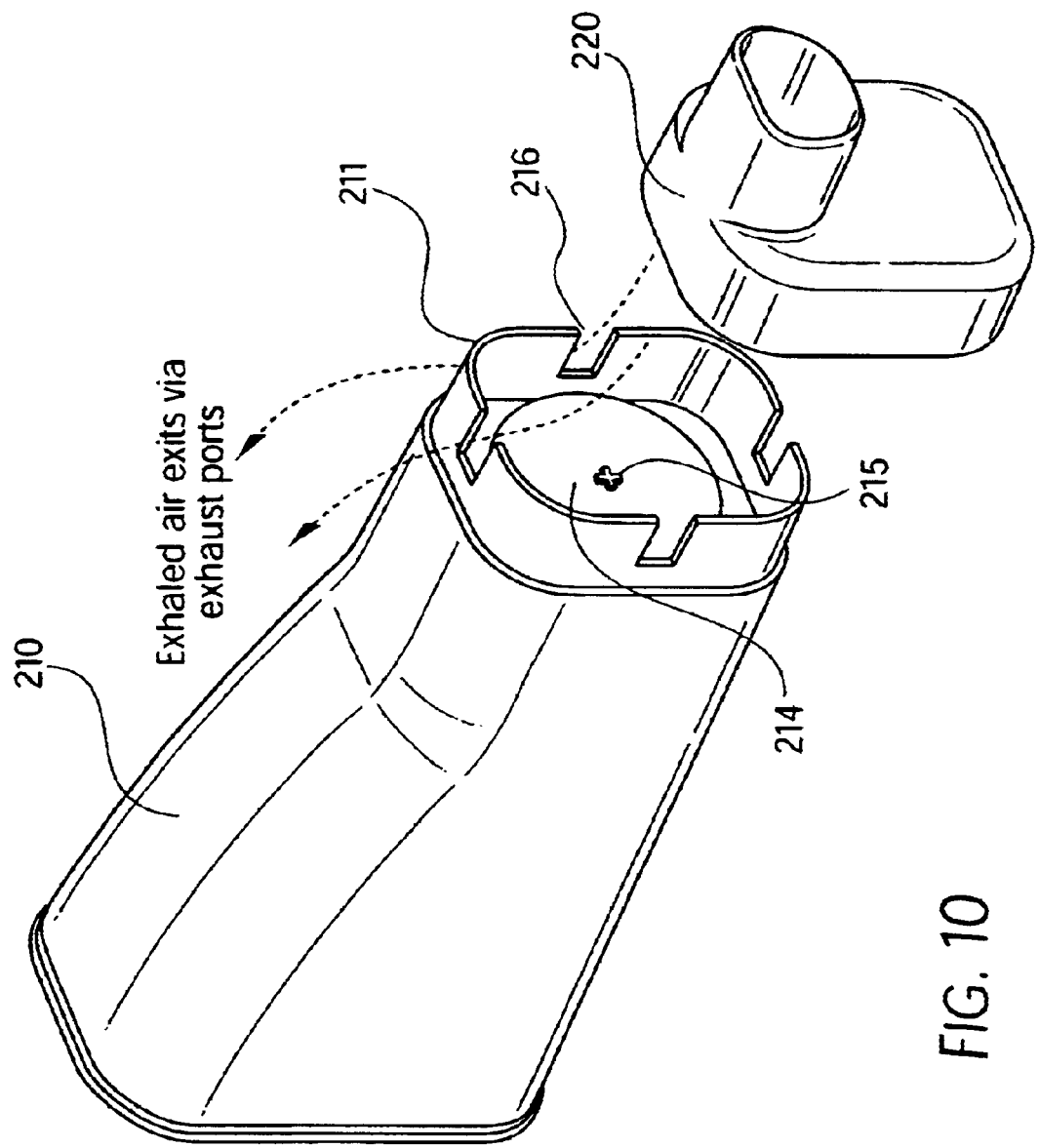
FIG. 10 shows a perspective view of one embodiment of a mouthpiece comprising a flexible, elastic material, which is not engaged onto the chamber body of the canister inhaler.
Figure 11:
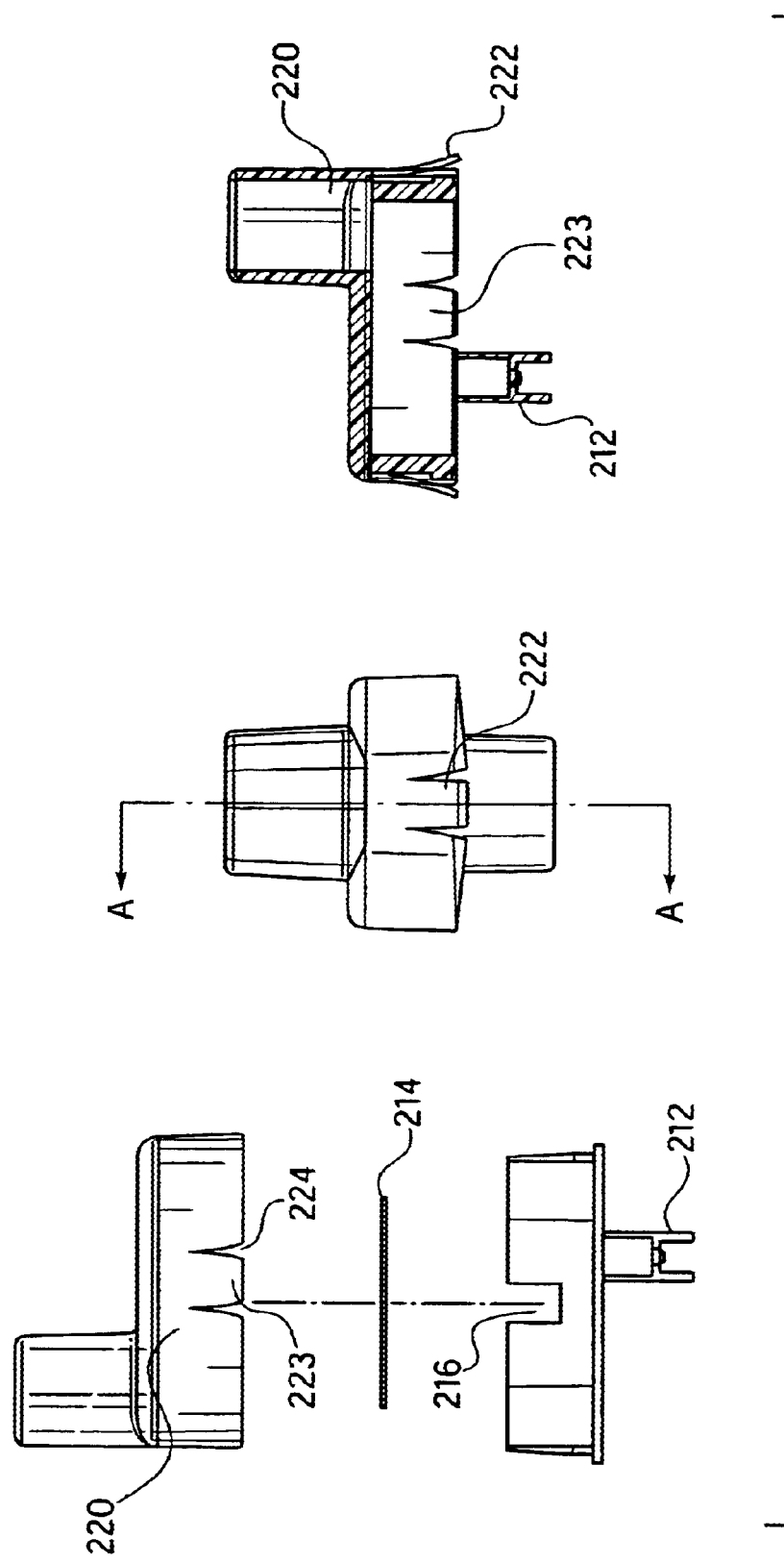
FIG. 11 shows the mouthpiece and the optional valve mechanism, including exhalation flaps in the mouthpiece, which exhalation flaps are each defined by two slits in the flexible, elastic material of the mouthpiece.
Figure 12:
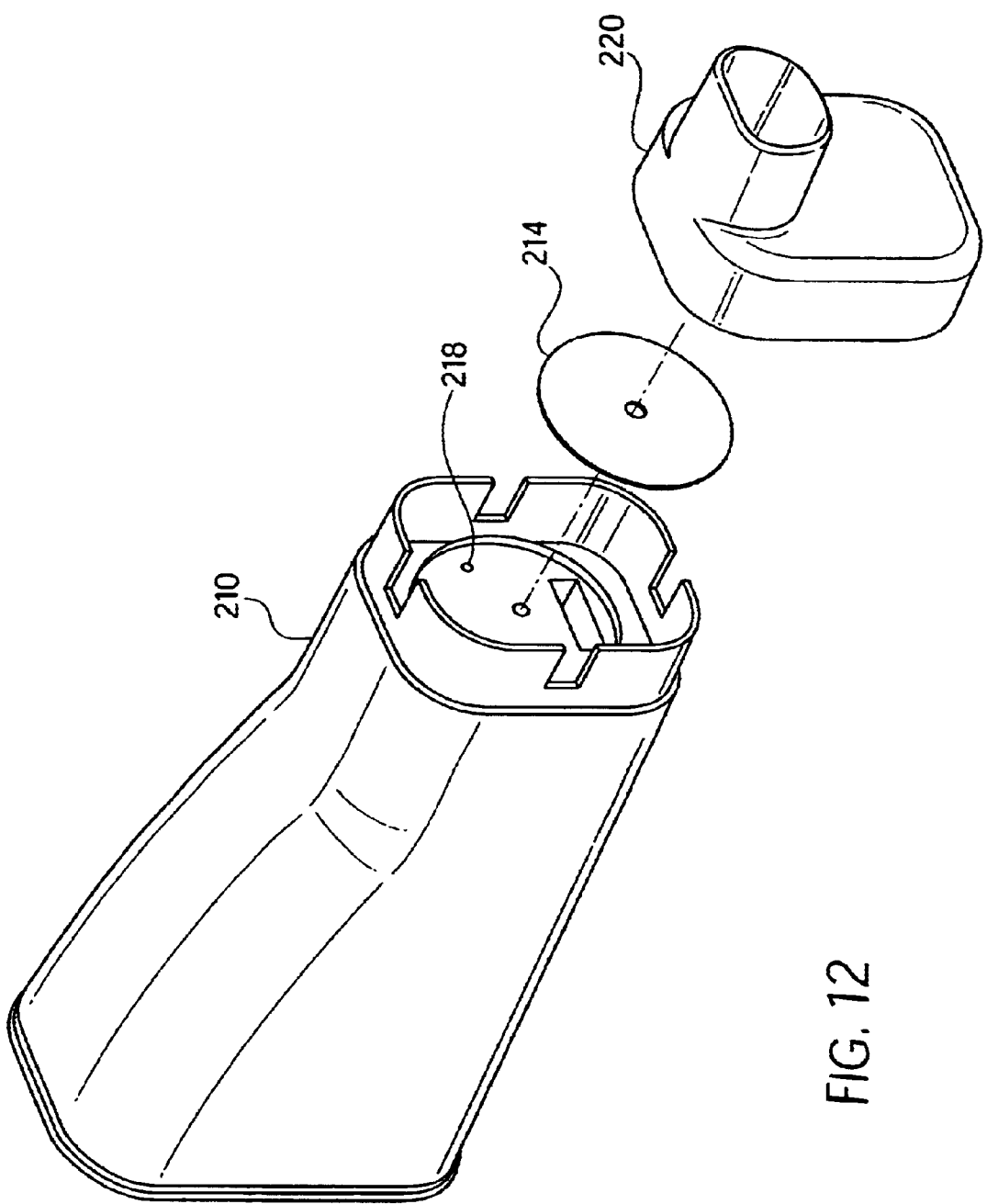
FIG. 12 shows an exploded, perspective view of the mouthpiece, the diaphragm valve and the chamber body, wherein the optional valve mechanism is visible within the chamber body, including at least one inhalation vent and four exhaust ports.

Another preferred embodiment of the invention has a mouthpiece made from a flexible, elastic material. In an alternative embodiment, a portion of the mouthpiece is made from a flexible, elastic material. In the latter embodiment, the flexible, elastic material is the portion of the mouthpiece that engages the chamber body, covering the exhaust port or ports. The exhaust port or ports are located in the surface of the chamber body. One embodiment is shown in FIG. 9. In this embodiment, the flexible, elastic material is silicone rubber, LSR 2050 from Bayer, which had a thickness sufficiently rigid to be useful as a mouthpiece, and sufficiently flexible that the portion of the mouthpiece covering the exhaust vents in the chamber body allowed air to escape from the mouthpiece during exhalation of the patient at a reasonable pressure.

In this embodiment, the inhaler accommodates at least one canister and comprises a cowling, a housing, a chamber body, a lever arm, and a mouthpiece. The cowling comprises a support structure and at least one canister receptor. The canister receptor can have a flexible fitting and a ring with the flexible fitting supported within the ring. The ring can be fixed in one end of the support structure, with the opposite end of the support structure open, allowing the patient to insert at least one canister into the cowling. The shape of the inner surface of the cowling is selected to guide each canister into the canister receptor, and can also be used to hold each canister in place within the cowling.

The housing comprises a chamber receiving section, a cowling receiving section, a support, a fresh air inlet, a compression spray outlet compression mechanism, and an enclosed passage. The cowling can be fixedly seated in the cowling receiving section, which has at least one cowling receiving section inlet port, and each compression spray outlet of each canister extends through the corresponding flexible fitting of the cowling, through the corresponding cowling receiving section inlet port, and into the enclosed passage of the housing. The enclosed passage is defined by the surfaces of the housing and ends in the chamber receiving section, which can be merely an opening in the housing.

Figure 13:
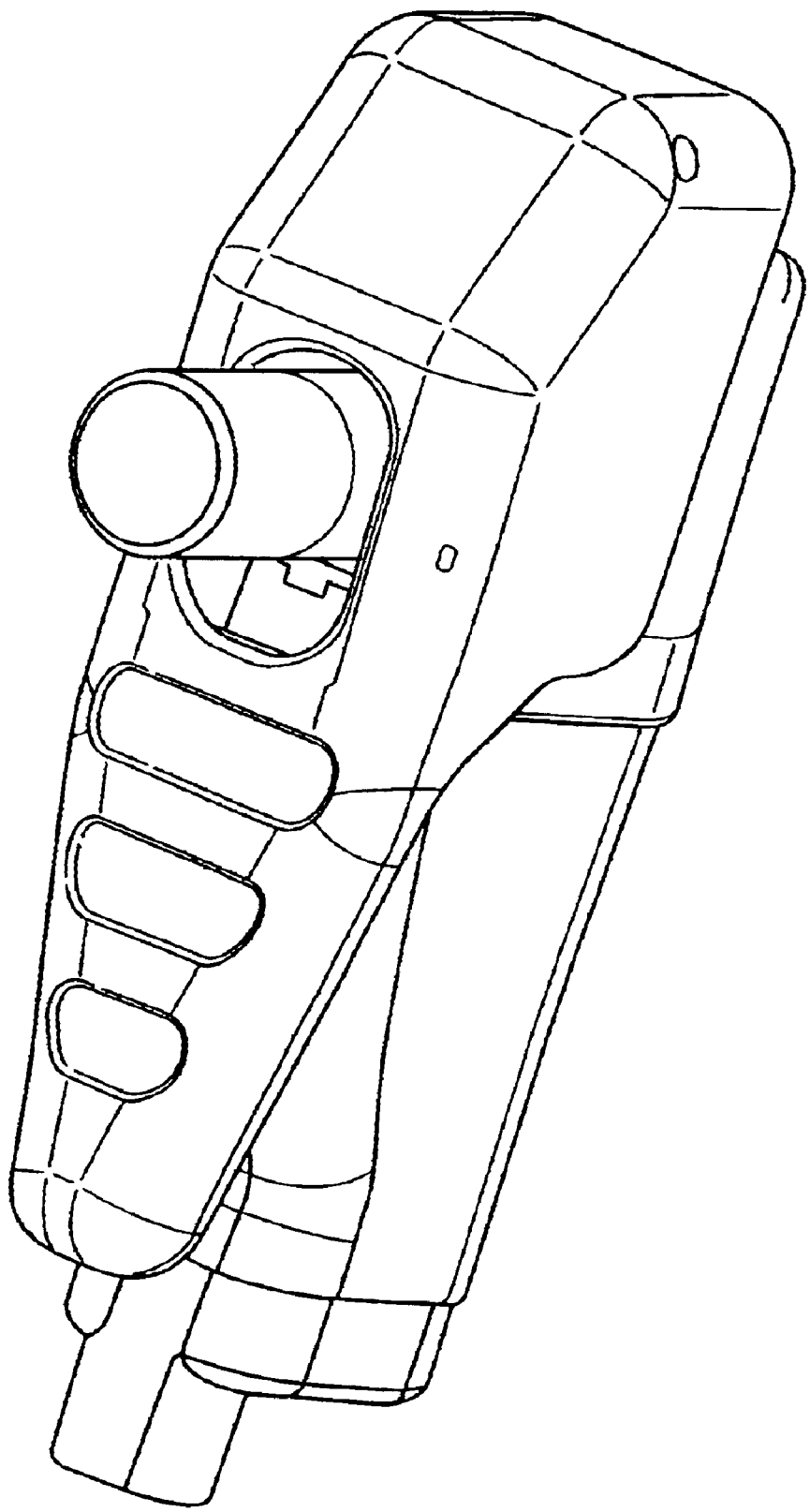
FIG. 13 shows an perspective view of one embodiment of the invention, having a single MDI canister.

The actuator lever has a lever arm and a distal end, which is pivotally mounted on the support of the housing. The distal end engages a canister when the actuator lever is depressed by a patient. In one embodiment, the distal end can engage the canister. In one alternative example of this embodiment, the distal end engages a separate engaging member, and the separate engaging member engages the canister. In one example of this alternative embodiment, the separate engaging member is a half-moon shaped coupler that is interposed between the actuator lever and the canister. This example is shown in FIG. 13. In yet another embodiment, the separate engaging member is a sliding selector switch, and the patient can select the mode of operation by positioning the sliding selector switch. In this embodiment the modes of operation can comprise either engaging a single canister or not engaging a single canister, or alternatively, the modes of operation can comprise engaging additional canisters or a locking position. In another example of this embodiment, the distal end engages the canister directly. Additional modes of operation are also possible, including but not limited to the engaging of multiple canisters simultaneously, and a sliding selector switch that can activate these modes is within the scope of the invention. In one embodiment, the sliding selector switch slides back and forth. In an alternative embodiment, the sliding selector switch slides side to side. In yet another embodiment, the sliding selector switch slides in rotation.

The mouthpiece has one end shaped to fit in a patient's mouth and the other end is shaped to fit on the chamber body. In one embodiment, the flexible, elastic material of the mouthpiece stretches over the exterior of the chamber body. The chamber body comprises a shell, which further comprises a mouthpiece mating section and a housing mating section. The housing mating section is an opening in the chamber body, and chamber body joins the mouthpiece to the housing. The housing mating section of the chamber engages the chamber receiving section of the housing.

In a typical embodiment, the chamber body opposes the actuator lever, and the patient can depress the actuator lever by squeezing the lever arm to the chamber body, causing the compression spray outlet of at least one canister to activate, spraying medication into the enclosed passage of the housing and the chamber body. There the medication mixes with air. When the patient inhales through the mouthpiece, fresh air enters the enclosed passage through the fresh air inlet of the housing, and the mixture of air and medication in the enclosed passage of the housing and the chamber body is drawn into the lungs of the patient.

In one preferred embodiment, the chamber further comprises a valve assembly. The valve assembly comprises a diaphragm valve and a valve body. The valve body is fixed in the chamber body. When the patient inhales, the diaphragm valve opens, because the pressure in the mouthpiece is less than the pressure in the chamber, causing the diaphragm valve to deflect, allowing air and medication to enter into the mouthpiece. When the patient exhales, the pressure in the mouthpiece is greater than the pressure in the chamber, and the diaphragm valve shuts against the valve body, which completely blocks the entry of exhaled air into the chamber body. The pressure in the mouthpiece exerts a hydrostatic pressure against the diaphragm valve, the valve body, and the mouthpiece. When the pressure exceeds a desired exhalation pressure, at least a portion of the flexible, elastic material of the mouthpiece is deflected from contacting the chamber body, and the exhaled air escapes from the mouthpiece. In one embodiment of the invention, the chamber body comprises exhalation ports, which are openings in the chamber body defined by the solid shell of the chamber body. The distance from the edge of the flexible, elastic material of the mouthpiece and an exhaust port is less than the distance from the edge of the chamber body and the edge of the flexible, elastic material; therefore, the air selectively escapes from the mouthpiece at the exhaust ports.

In an alternative embodiment, the valve assembly is located in the chamber body, but is located closer to the housing mating section. In this embodiment, the exhaled air still exits from the exhaust vents in the mouthpiece mating section of the chamber body. Nevertheless, the exhaled air does not readily mix with the air in the chamber body before it exits through the exhaust ports. In this embodiment, a structured exhaust vent can be used that directs exhaled air from the mouthpiece to the exhaust ports. For example, one or more channels may lead from the mouthpiece to one or more exhaust ports, whereby exhaled air predominantly exits the exhaust ports by flowing through the channel or channels.

A preferred embodiment of the mouthpiece uses silicone rubber and has a thickness of silicone rubber in the range between about 0.5 mm and 5 mm. In one preferred embodiment silicone rubber GE6050 was used. Preferably, the thickness of silicone rubber GE6050 was between about 0.5 mm and 5 mm, depending on the type of exhaust venting, retention devices, and the location and size of exhaust flaps, if any. Also preferably, the exhalation pressure was less than 2 inches of water above ambient pressure. In another preferred embodiment, silicone rubber LSR2050 from Bayer was used.

In an alternative embodiment, the thickness of the flexible, elastic material can be substantially a constant thickness. By substantially a constant thickness, the inventors mean that the thickness of the flexible, elastic material is the same, within reasonable manufacturing limits, in the end that the patient inserts into his or her mouth as it is at the end that is stretched over the chamber body.

In another alternative embodiment, the thickness of the flexible, elastic material can be reduced at the portion of the mouthpiece covering the exhaust vents in the chamber body, whereby a very low exhaust pressure is able to open the exhaust vents, allowing exhaust air to escape the mouthpiece. A preferred embodiment has an abrupt transition between the thicker material at the end of the mouthpiece that is inserted into a patient's mouth and the thinner material that covers the exhaust ports.

In one alternative embodiment, the flexible, elastic material can taper from thicker material at the end of the mouthpiece that inserts into the patients mouth to the end of the mouthpiece covering the exhaust vents in the chamber body. In a preferred embodiment, this tapered transition occurs over a distance no greater than 1 cm, which was the length of the mouthpiece receiving section of the chamber body in one particular embodiment of the chamber body.

In yet another alternative embodiment, the thickness of the flexible, elastic material can be reduced in only a small region surrounding and including the flexible, elastic material covering the exhaust vent or exhaust vents in the chamber body. In this embodiment, it is possible that the thicker flexible, elastic material can constrain the thinner flexible, elastic material. In one alternative, the surface area dimension of the thin region surrounding the exhaust port in the chamber body is selected in combination with the thicknesses of the flexible elastic material to achieve an exhaust pressure that is desired for opening the exhaust ports. In another alternative, two slits in the flexible elastic material separate the thinner flexible, elastic material of an exhaust flap from the thicker flexible, elastic material of the remainder of the mouthpiece, except at the base of the exhaust flap. In yet another embodiment of the invention, the slits were used with no transition in the thickness of the flexible, elastic material, and this also reduced the exhaust pressure required to cause exhaled air to exit through the exhaust port or ports.

The exhaust flaps cover the exhaust ports, but deflect during exhalation, allowing exhaled air to escape between the exhaust flap and the chamber body. In a more general embodiment of the invention, the mouthpiece comprises one or a plurality of exhaust tabs, wherein exhaust tabs can be defined as any flexible elastic material of the mouthpiece that covers an exhaust port, but either extends beyond the rest of the mouthpiece or is separated from the surrounding flexible, elastic material of the mouthpiece by any gap, removal of material or slit.

In a preferred embodiment of the invention, the flexible, elastic material of the mouthpiece has a substantially constant thickness, and the mouthpiece has one or a plurality of exhaust flaps covering the exhaust ports. These exhaust flaps are tabs of flexible, elastic material that are not constrained by the rest of the mouthpiece, except at the base of the exhaust flaps, where the exhaust flaps are integrally or fixedly attached to the rest of the mouthpiece. Therefore, the pressure for allowing the exhaled air to escape can be reduced compared to a mouthpiece without separately or integrally attached exhaust flaps.

In one alternative embodiment of the invention, a retaining ring was placed around the outside of the mouthpiece where the mouthpiece engaged the chamber body. This retaining ring served to hold the mouthpiece onto the chamber body; however, the retaining ring did not interfere with the exhaust port. In one embodiment, the retaining ring was an elastic ring. In another embodiment, the retaining ring was a rigid plastic strap that could be tightly affixed, holding the mouthpiece onto the chamber body. In yet another embodiment the retaining ring was a clamp. In a possible embodiment, the retaining ring is positioned such that it overlaps a groove in the chamber body, securely fastening the flexible mouthpiece to the chamber body. Alternatively, the chamber body can have two continuous, concentric raised projections that fix the retaining ring in position. Yet another alternative for fixing the position of the retaining ring with relation to the chamber body is to provide several raised protrusions instead of continuous, concentric raised projections to fix the retaining ring in position.

In one embodiment of the invention, the exhaust port is a surface opening of a structured exhaust vent. The structured exhaust vent can be included for structural rigidity, as a mechanism for directing exhaled air to the exhaust ports reducing unwanted mixing of exhaust air and air within the mouthpiece or chamber body, and/or for improved functioning of the opening and closing of the flexible, elastic material of the mouthpiece. For example, one embodiment directs the exhaust air to the very end of one or more exhaust flaps, such that the exhaust air preferentially deflects only the very end of the exhaust flap, reducing the incidence of acoustic emissions or unwanted noise during exhalation. In another embodiment, the use of a structured exhaust vent uses channels in the mouthpiece to direct exhaled air to the exhaust ports. By using channels, this embodiment avoids the mixing of exhaled air with the air in the chamber body, and allows the inhalation vent to be located in the housing at the fresh air inlet, rather than in the chamber body. Alternatively, the inhalation vent can be located in the chamber body, but closer to the housing mating section.

Although the foregoing invention has been described in some detail by way of illustration and example for purposes of clarity and understanding, it will be obvious to one of ordinary skill in the art that various modifications and changes which are within the knowledge of those skilled in the art are considered to fall within the scope of the present invention.

What is claimed is:

1. An inhaler for delivery of medication from a single MDI canister, the MDI canister having a spray outlet, to the lungs of a patient after the patient actuates the MDI canister using the patient's hand and inhales the medication in one or more breaths through the patient's mouth, comprising:

a universal MDI canister receiving section;

a housing, the housing comprising an air inlet and an enclosed passage, wherein the universal canister receiving section allows the MDI canister spray outlet to be inserted into the housing, such that medication from the MDI canister enters the enclosed passage, when the MDI canister is actuated by the patient;

a chamber body comprising a housing mating end, a shell defining the chamber body, wherein the chamber body extends out from the housing, and a mouthpiece mating end, wherein the chamber body is fixedly attached to the housing at the housing mating end, and wherein the mouthpiece mating end comprises at least one exhaust port;

an inhalation valve, wherein the inhalation valve is fixed in the chamber body, wherein the inhalation valve allows inhalation of air by the patient, and wherein the inhalation valve blocks exhaled air from the patient from entering the chamber body;

a mouthpiece comprising a first end, wherein the first end is shaped to fit in the patient's mouth, and a distal end, opposed to the first end, and wherein the distal end is comprised of a flexible, elastic material, wherein the distal end elastically extends over the mouthpiece mating end and fixedly engages the mouthpiece mating end, wherein the flexible, elastic material of the distal end covers the at least one exhaust port of the mouthpiece mating end of the chamber body; and an actuator lever having a lever arm and a distal end, wherein the distal end is pivotally mounted to the housing and wherein the lever arm opposes the chamber body, and wherein the actuator lever engages the single MDI canister, actuating the MDI canister, when the actuator lever is actuated by the patient's hand closing on the lever arm and the chamber body, wherein medication exits from the spray outlet of the MDI canister, enters the housing, and is drawn into the chamber body by the inhalation of the patient, whereby it mixes with air, and flows through the mouthpiece, through the patient's mouth, and into the lungs of the patient in one or more breaths.

2. The inhaler of claim 1, wherein the inhalation valve comprises a diaphragm valve and a valve body, wherein the diaphragm valve opens during inhalation and closes against the valve body during exhalation, preventing exhaled air from entering the chamber body.

3. The inhaler of claim 1, wherein the flexible, elastic material of the distal end of the mouthpiece comprises at least one flexible tab, wherein the at least one flexible tab covers the at least one exhaust port during inhalation and deflects during exhalation by the patient, whereby exhaust air escapes from between the flexible, elastic material of the mouthpiece and the chamber body.

4. The inhaler of claim 3, wherein the exhalation pressure necessary to open the exhaust tap is less than 2 inches of water above ambient pressure.

5. The inhaler of claim 3, further comprising a retaining ring, wherein the retaining ring couples the mouthpiece to the chamber body.

6. A mouthpiece for a spacer with an exhalation valve mechanism for use by a patient to inhale medication, comprising:

a flexible, elastic material;

a first end; and a distal end, wherein the distal end is shaped to fit the mouth of the patient, and wherein the first end is shaped to elastically and fixedly engage a spacer, and wherein air exhaled by the patient exits the mouthpiece by passing between the flexible, elastic material of the mouthpiece and the spacer via a flap formed by slits in the flexible, elastic material of the mouthpiece.

7. The mouthpiece of claim 6, wherein the first end has at least one exhalation tab formed by the flap.

8. The mouthpiece of claim 6, wherein the flexible, elastic material is selected from the group of flexible, elastic materials consisting of silicone rubber, neoprene rubber, butyl rubber and latex.

9. The mouthpiece of claim 8, wherein the flexible elastic material is silicone rubber.

10. The mouthpiece of claim 9, wherein the thickness of the silicone rubber is selected to be in a range between 0.5 mm and 5 mm.

11. The mouthpiece of claim 9, wherein the exhaust pressure that causes air to escape from the mouthpiece is less than 2 inches of water above ambient pressure.

12. An inhaler for delivery of medication from at least one MDI canister comprising the mouthpiece of claim 6.

13. A mouthpiece for a spacer with an exhalation valve mechanism for use by a patient to inhale medication in more than one breath, comprising:

a flexible, elastic material;

a first end; and a distal end, wherein the distal end is shaped to fit the mouth of the patient, and wherein the first end is shaped to elastically and fixedly engage and maintain the mouthpiece in position on a spacer, wherein air exhaled by the patient exits the mouthpiece by passing between the flexible, elastic material of the mouthpiece and the spacer, and wherein both the first end and the distal end are comprised of the flexible, elastic material, and wherein the flexible, elastic material of the patient end is thicker than the flexible, elastic material of the first end.

14. The mouthpiece of claim 13, wherein the change in thickness occurs abruptly.

15. The mouthpiece of claim 13, wherein the change in thickness transitions over a distance of at least 1 cm.

16. An inhaler for delivery of medication from at least one canister to the lungs of a patient by inhalation through the patient's mouth, the at least one canister has a compression spray outlet, the inhaler comprising:

a cowling having a support structure including a flexible fitting, wherein the support structure has a first end, an opposite end, an inner surface, and an outer surface, wherein the opposite end of the support structure is open, allowing the patient to insert at least one canister into the cowling, and wherein the shape of the inner surface of the cowling and the flexible fitting is selected to guide each canister into the first end, and to sealingly hold each canister in place within the cowling;

a housing, wherein the housing further comprises a chamber receiving section, a cowling receiving section, a support, a fresh air inlet, at least one compression spray outlet compression mechanism, and an enclosed passage, and wherein the cowling is fixedly seated in the cowling receiving section, and wherein the cowling receiving section has at least one cowling receiving section inlet port, and wherein, the compression spray outlet of the at least one canister extends through the corresponding cowling receiving section inlet port, and into the enclosed passage of the housing, and wherein the enclosed passage is defined by the surfaces of the housing and ends in the chamber receiving section, wherein the chamber receiving section is an opening in the housing;

an actuator lever having a lever arm and a distal end, wherein the distal end is pivotally mounted on the support of the housing, whereby the distal end engages at least one canister, when the actuator lever is depressed by the patient;

a mouthpiece comprising a first end, wherein the first end is shaped to fit in the patient's mouth and a distal end, opposed to the first end, and wherein the distal end is comprised of a flexible, elastic material;

a chamber further comprising a mouthpiece mating section, a chamber body and a housing mating section, wherein the housing mating section comprises a first opening in the chamber body, wherein the chamber body comprises a shell, and wherein the mouthpiece mating section comprises a second opening in the chamber body, and wherein the distal end of the mouthpiece engages the mouthpiece mating section of the chamber body, and wherein the housing mating section of the chamber engages the chamber receiving section of the housing, and wherein the chamber body opposes the actuator lever, whereby the patient can depress the actuator lever by squeezing the lever arm to the chamber body, and whereby the compression spray outlet of at least one canister is activated, whereby medication enters into the enclosed passage of the housing and the chamber body, and whereby, when the patient inhales through the mouthpiece, fresh air enters the enclosed passage through the fresh air inlet of the housing, whereby the mixture of air and medication in the enclosed passage of the housing and the chamber body is drawn into the lungs of the patient.

17. The inhaler of claim 16, wherein the chamber further comprises a valve assembly, and wherein the valve assembly is fixed in the chamber body, and wherein the valve assembly opens during inhalation and closes against the valve body during exhalation, whereby medication and air are prevented from exiting through the valve assembly.

18. The inhaler of claim 17, wherein the valve assembly is fixed in the chamber body, and wherein the valve assembly comprises a diaphragm valve and a valve body, wherein the diaphragm valve opens during inhalation and closes against the valve body during exhalation, preventing exhaled air from entering the chamber body.

19. The inhaler of claim 17, wherein the mouthpiece mating section of the chamber body has at least one exhaust port, and wherein the flexible, elastic material of the distal end of the mouthpiece is selected to deflect at the at least one exhaust port during exhalation by the patient, whereby exhaust air escapes from between the flexible, elastic material of the mouthpiece and the chamber body during exhalation.

20. An inhaler for delivering medication from an MDI canister having a spray outlet, comprising:

an MDI canister receiving section;

a housing coupled to the canister receiving section and having an air inlet, an enclosed passage and a mouthpiece mating end, wherein the canister receiving section allows the MDI canister spray outlet to be inserted into the housing, and wherein the mouthpiece mating end comprises at least one exhaust port;

an inhalation valve, wherein the inhalation valve is fixed inside the housing, wherein the inhalation valve allows inhalation of air by the patient, and wherein the inhalation valve blocks exhaled air from the patient from entering the housing;

a mouthpiece comprising a first end shaped to fit in the patient's mouth, and a distal end opposed to the first end, wherein the distal end is coupled to the mouthpiece mating end so as to cover the at least one exhaust port of the mouthpiece mating end of the housing; and an actuator lever having a distal end pivotally mounted to the housing and a lever arm opposed to the housing, wherein the actuator lever engages the MDI canister so as to actuate the MDI canister when the actuator lever is actuated.

21. The inhaler of claim 20, wherein the inhalation valve comprises a diaphragm valve and a valve body, wherein the diaphragm valve opens during inhalation and closes against the valve body during exhalation, preventing exhaled air from entering the housing.

22. The inhaler of claim 20, wherein the distal end of the mouthpiece comprises at least one flexible exhaust tab, wherein the at least one flexible exhaust tab covers the at least one exhaust port during inhalation and deflects during exhalation by the patient, whereby exhaust air escapes from between the mouthpiece and the housing.

23. The inhaler of claim 22, wherein the exhalation pressure necessary to open the exhaust tab is less than 2 inches of water above ambient pressure.

24. The inhaler of claim 22, further comprising a retaining ring, wherein the retaining ring couples the mouthpiece to the housing.

25. A mouthpiece for an inhaler device with an exhalation valve mechanism for use by a patient to inhale medication, comprising:

a first end made of flexible, elastic material; and a distal end, wherein the distal end is shaped to fit the mouth of the patient, and wherein the first end is shaped to engage and maintain the mouthpiece in position on an exhaust port of the inhaler device, and wherein air exhaled by the patient exits the mouthpiece by passing between the flexible, elastic material of the first end and the exhaust port of the inhaler device.

26. The mouthpiece of claim 25, wherein the first end has at least one exhalation tab.

27. The mouthpiece of claim 25, wherein the flexible, elastic material is selected from the group of flexible, elastic materials consisting of silicone rubber, neoprene rubber, butyl rubber and latex.

28. The mouthpiece of claim 27, wherein the flexible elastic material is silicone rubber.

29. The mouthpiece of claim 28, wherein the thickness of the silicone rubber is selected to be in a range between 0.5 mm and 5 mm.

30. The mouthpiece of claim 28, wherein an exhaust pressure that causes air to escape from the mouthpiece is less than 2 inches of water above ambient pressure.

31. The mouthpiece of claim 25, wherein both the first end and the distal end are comprised of the flexible, elastic material, and wherein the flexible, elastic material of the distal end is thicker than the flexible, elastic material of the first end.

32. The mouthpiece of claim 31, wherein the change in thickness occurs abruptly.

33. The mouthpiece of claim 31, wherein the change in thickness transitions over a distance of at least 1 cm.

34. An inhaler for delivery of medication from at least one MDI canister comprising the mouthpiece of claim 25.

* * * * *